(12) United States Patent
Kim et al.

(10) Patent No.: US 6,524,564 B1
(45) Date of Patent: Feb. 25, 2003

US006524564B1

(54) URETHANE(METH)ACRYLATES CONTAINING SILOXANE GROUPS AND ABLE TO UNDERGO FREE-RADICAL POLYMERIZATION

(75) Inventors: Son Nguyen Kim, Hemsbach (DE); Axel Sanner, Frankenthal (DE); Volker Schehlmann, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,929

(22) PCT Filed: Aug. 25, 1999

(86) PCT No.: PCT/EP99/06234

§ 371 (c)(1),
(2), (4) Date: Feb. 14, 2001

(87) PCT Pub. No.: WO00/12588

PCT Pub. Date: Mar. 9, 2000

(30) Foreign Application Priority Data

Aug. 26, 1998 (DE) .......................................... 198 38 852
May 20, 1999 (DE) .......................................... 199 23 276

(51) Int. Cl.$^7$ .......................... A16K 7/11; C08F 30/08; C08L 83/08
(52) U.S. Cl. ................. 424/70.12; 424/70.11; 424/70.16; 424/70.31; 424/401; 514/63; 514/476; 514/478; 525/100; 526/279; 528/25; 528/26; 528/28; 528/44; 528/75
(58) Field of Search ................ 424/70.12, 70.11, 424/70.16, 78.31, 401; 514/63, 476, 478; 526/279; 528/25, 26, 28, 44, 75; 525/100

(56) References Cited

U.S. PATENT DOCUMENTS

| | | | |
|---|---|---|---|
| 4,130,708 A | * 12/1978 | Friedlander et al. | 522/172 |
| 4,486,577 A | * 12/1984 | Mueller et al. | 351/160 H |
| 4,690,683 A | 9/1987 | Chien et al. | 604/896 |
| 4,762,887 A | 8/1988 | Griswold et al. | 522/99 |
| 4,786,657 A | * 11/1988 | Hammer et al. | 522/148 |
| 5,162,472 A | 11/1992 | O'Lenick, Jr. et al. | 526/279 |
| 5,166,276 A | 11/1992 | Hayama et al. | 525/329 |
| 5,334,372 A | 8/1994 | Kawamata et al. | 424/78 |
| 5,472,686 A | 12/1995 | Tsubaki et al. | 424/59 |
| 5,618,524 A | 4/1997 | Bolich, Jr. et al. | 424/70 |
| 5,643,581 A | 7/1997 | Mougin et al. | 424/401 |
| 5,650,159 A | 7/1997 | Lion et al. | 424/401 |
| 6,093,384 A | 7/2000 | Lion et al. | 424/45 |
| 6,166,093 A | 12/2000 | Mougin et al. | 514/772 |

FOREIGN PATENT DOCUMENTS

| | | |
|---|---|---|
| CA | 2011246 | 9/1990 |
| CA | 2148805 | 6/1994 |
| CA | 2189886 | 5/1997 |
| DE | 42 25 045 | 2/1994 |
| DE | 195 24 816 | 1/1997 |
| DE | 195 41 326 | 5/1997 |
| EP | 705594 | 4/1996 |
| WO | WO 93/03703 | 3/1993 |
| WO | WO 94/03515 | 2/1994 |
| WO | WO 95/00108 | 1/1995 |
| WO | WO 97/00664 | 1/1997 |
| WO | WO 97/17386 | 5/1997 |
| WO | WO 97/25021 | 7/1997 |
| WO | 97/38035 | 10/1997 |

OTHER PUBLICATIONS

"Novel Polyurethane–Silicone Hydrogels", Yu–Chin Lai, Journal of Applied Polymer Science, (1995) 56,201, John Wiley & Sons Inc.*

* cited by examiner

*Primary Examiner*—Robert Dawson
*Assistant Examiner*—Marc S Zimmer
(74) *Attorney, Agent, or Firm*—Keil & Weinkauf

(57) ABSTRACT

The present invention relates to free-radically polymerizable, siloxane-containing urethane (meth) acrylates which comprise, in incorporated form, a) at least one compound which contains at least one active hydrogen atom and at least one free-radically polymerizable $\alpha,\beta$-ethylenically unsaturated double bond per molecule, b) at least one diisocyanate, c) at least one compound which contains two active hydrogen atoms per molecules, d) at least one compound which contains at least one active hydrogen atom and at least one siloxane group per molecule, to water-soluble or water-dispersible polymers which comprise these urethane (meth)acrylates in copolymerized form, to the use of these polymers, and to cosmetic compositions which comprise these polymers.

11 Claims, No Drawings

URETHANE(METH)ACRYLATES CONTAINING SILOXANE GROUPS AND ABLE TO UNDERGO FREE-RADICAL POLYMERIZATION

The present invention relates to free-radically polymerizable, siloxane-containing urethane (meth) acrylates, to water-soluble or water-dispersible polymers which comprise these in copolymerized form, to the use of these polymers, and to cosmetic compositions which comprise these polymers.

In cosmetology, polymers having film-forming properties are used for setting, shaping and improving the structure of the hair. These hair-treatment compositions generally comprise a solution of the film former in an alcohol or a mixture of alcohol and water.

Hair-setting compositions are generally sprayed onto the hair in the form of aqueous-alcoholic solutions. After the solvent has evaporated, the hair is held in the desired shape at the mutual points of contact by the polymer which remains. The polymers should on the one hand be hydrophilic so that they can be washed out of the hair, but on the other hand should be hydrophobic so that the hair treated with the polymers retains its shape, even when atmospheric humidity is high, and does not stick together. In order to achieve as efficient a hair-setting action as possible, it is furthermore desirable to use polymers which have a relatively high molecular weight and a relatively high glass transition temperature (at least 15° C.).

When formulating hair-setting compositions, another consideration is that because of the environmental regulations governing the emission of volatile organic compounds (VOCS) into the atmosphere, it is necessary to reduce the content of alcohol and of propellant.

A further current demand on hair-treatment compositions is that they should impart to the hair a natural appearance and shine even, for example, when the hair concerned is by its own nature particularly thick and/or dark.

It is known to use polysiloxanes and polysiloxane derivatives, which are not bonded covalently to a setting polymer, as softening component in haircare compositions. Since silicone oils and polysiloxane derivatives are incompatible with setting polymers, which generally contain polar groups, the preparation of stable formulations generally requires the addition of other auxiliaries. Nevertheless, there are frequent instances of separation during storage or after the products have been applied to the hair. The application range of such formulations is thus severely limited. In order to prevent the disadvantageous separation, attempts have been made to bond polysiloxane groups covalently to the setting polymer.

WO-A-97/00664 describes aqueous nail varnishes which comprise a crosslinked acrylic resin based on difunctional urethane acrylate oligomers. The films obtained with these resins are neither soluble in water nor redispersible in water. Use in hair cosmetics, in particular as setting polymer, is not described in this document. The use of siloxane-containing urethane acrylates is not described either.

EP-A-408 311 describes the use of a copolymer which comprises, in incorporated form, a) an ethylenically unsaturated, hydrophilic monomer, b) an ethylenically unsaturated monomer containing polysiloxane groups and c) an ethylenically unsaturated, hydrophobic monomer, in haircare products.

EP-A-412 704 describes a haircare composition based on a graft copolymer which has monovalent siloxane polymer units on a backbone based on a vinyl polymer.

WO 93/03703 describes a hairspray composition comprising: a) a surface-active composition, b) an ionic resin having a number-average molecular weight of at least 300,000 and c) a liquid carrier. Here, the ionic resin can be the graft copolymers described in EP-A-412 704.

EP-A-362 860 describes alcohol-modified silicone ester derivatives and cosmetic compositions comprising them. None of these publications describes setting polymers based on $\alpha,\beta$-ethylenically unsaturated polyurethanes which additionally have at least one siloxane group.

It is known to use polyurethanes with film-forming properties in cosmetics. For example, DE-A-42 25 045 and WO 94/03515 describe the use of water-soluble or water-dispersible, anionic polyurethanes as hair-setting compositions. DE-A-42 41 118 describes the use of cationic polyurethanes and polyureas as auxiliaries in cosmetic and pharmaceutical preparations. These polyurethanes do not include polysiloxane groups and can only partially satisfy the requirements for hair-setting polymers.

Thus, for example, the suppleness of the hair is in need of improvement.

EP-A-492 657 describes a cosmetic composition for use in skincare and haircare products, which comprises a linear polysiloxane-polyoxyalkylene block copolymer.

EP-A-0 389 386 describes block copolymers which comprise, in incorporated form, a polysiloxanediol, a block copolyester and a diisocyanate. They are suitable for the controlled release of active ingredients.

EP-A-227 816 describes polydimethylsiloxanes with two hydroxyl groups at one end of the chain and a trimethylsilyl group at the other end, of the formula

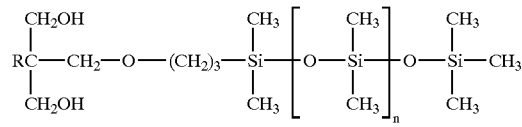

in which R is hydrogen, methyl or ethyl, and n is from 0 to 4000, and also polyurethanes modified therewith. These siloxane-modified polyurethanes are prepared by polycondensation of the polysiloxanes of the above formula with polyurethane prepolymers which have two or more isocyanate groups. Free-radically polymerizable siloxane-containing polyurethanes and polymers which comprise these in copolymerized form are not described. Use of the modified polyurethanes in hair cosmetics is not described either.

EP-A-636 361 describes a cosmetic composition which comprises, in a carrier, at least one pseudolatex based on a polycondensate which comprises at least one polysiloxane unit and at least one polyurethane and/or polyurea unit having anionic or cationic groups. These polycondensates do not have a free-radically polymerizable $\alpha,\beta$-ethylenically saturated double bond and likewise are not used for the silicone-modification of other polymers. The ability of these film formers to be washed out is unsatisfactory. In addition, because of their high siloxane content, they do not have the setting action necessary for a hair polymer either.

WO 97/25021 has a disclosure content comparable with that in EP-A-0 636 361.

EP-A-751 162 describes the use of polycondensates having polyurethane and/or urea units and condensed polysiloxane units or grafted-on polysiloxane side chains for the preparation of cosmetic or dermatological compositions. The components used correspond essentially to those described in EP-A-636 361.

EP-A-0 705 594 describes a cosmetic composition which comprises an aqueous dispersion of a film-forming polymer and a water-soluble or water-dispersible silicone composition. The film-forming polymer can be a polyurethane or a polyurea.

DE-A-195 24 816 describes hydroxylated siloxane block copolymers which comprise siloxane and hydrocarbon segments which are linked via hydroxylated hydrocarbon structures.

DE-A-195 41 326 and WO 97/17386 describe water-soluble or water-dispersible polyurethanes with terminal acid groups. For their preparation, a polyurethane prepolymer with terminal isocyanate groups is reacted with an aminosulfonic acid or aminocarboxylic acid. Here, the polyurethane prepolymers can also comprise, in condensed form, siloxane compounds having two groups which are reactive toward isocyanate groups, although the publication does not give an example of a corresponding polyurethane prepolymer.

DE-A-195 41 658 describes water-soluble or water-dispersible graft copolymers of a polyurethane prepolymer with terminal isocyanate groups and a protein containing amino groups, it also being possible for the prepolymer to contain siloxane groups in incorporated form.

Free-radically polymerizable, siloxane-containing polyurethanes and polymers which comprise these in copolymerized form are not described in the abovementioned documents.

EP-A-687 459 describes hair-treatment compositions based on an aqueous polymer dispersion which is obtainable by free-radical graft copolymerization of a monoethylenically unsaturated siloxane macromonomer and at least one polymer, which can be a polyester or polyesteramide. Free-radically unsaturated, siloxane-containing polyurethanes are not described. The reaction of the monoethylenically unsaturated siloxane macromers with other α,β-ethylenically unsaturated components is not described either.

EP-A-687 462 and U.S. Pat. No. 5,650,159 have a disclosure content which is comparable with that of EP 687 459, where the polymers which are graft-copolymerized with the siloxane macromonomers are polyurethanes and/or polyureas.

WO 95/00108 describes liquid hair-treatment compositions based on graft copolymers of a vinyl polymer backbone and silicone-containing macromers grafted thereon. The vinyl copolymer backbone consists here of a hydrophilic carboxyl-containing monomer and optionally a lipophilic monomer. Silicone-containing macromers which comprise diisocyanates in incorporated form are not described in this document.

U.S. Pat. No. 5,162,472 describes silicone-containing polymers obtainable by free-radical polymerization of a vinylsilicone-containing monomer, which can be (meth) acrylic esters of siloxane polyols or vinylsilicone urethanes based on benzene-1-(1-isocyanato-1-methylethyl)-3-(1-(methyl)ethynyl). Free-radically polymerizable siloxane-containing polymers based on diisocyanates are not described.

It is an object of the present invention to provide novel, free-radically polymerizable siloxane-containing urethane (meth)acrylates. These should be suitable for the preparation of siloxane-modified polymers by a free-radical polymerization. Preferably, the resulting siloxane-modified polymers should be suitable as hair-treatment compositions. In particular, these hair-treatment compositions should on the one hand be usable as hair-setting compositions, but on the other hand should also have a good ability to be washed out (redispersibility).

We have found that this object is achieved by free-radically polymerizable, siloxane-containing urethane (meth)acrylates which comprise, in incorporated form, at least one compound having at least one active hydrogen atom and at least one free-radically polymerizable α,β-ethylenically unsaturated double bond, at least one diisocyanate, at least one compound with 2 active hydrogen atoms per molecule and at least one compound containing at least one siloxane group per molecule.

The present invention therefore relates to free-radically polymerizable, siloxane-containing urethane (meth) acrylates which comprise, in incorporated form, a) at least one compound which contains at least one active hydrogen atom and at least one free-radically polymerizable α,β-ethylenically unsaturated double bond per molecule, b) at least one diisocyanate, c) at least one compound which contains two active hydrogen atoms per molecule, d) at least one compound which contains at least one active hydrogen atom and at least one siloxane group per molecule, and the salts thereof.

For the purposes of the present invention, the expression "urethane (meth)acrylate" also includes compounds which have urea groups instead of or in addition to the urethane groups. Urea groups result during the reaction of an isocyanate group with a primary or secondary amino group. For the preparation of urethane (meth)acrylates having urea groups, it is possible to use components containing active hydrogen atoms a), c) and/or d) and optionally e) and/or f) which comprise at least one compound having at least one primary and/or secondary amino group.

For the purposes of the present invention, the expression $C_1$- to $C_{30}$-'alkyl' includes straight-chain and branched alkyl groups. Examples of suitable short-chain alkyl groups are straight-chain or branched $C_1$–$C_8$-alkyl, preferably $C_1$–$C_6$-alkyl and particularly preferably $C_1$–$C_4$-alkyl groups. In particular, these include methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

Suitable longer-chain $C_8$- to $C_{30}$-alkyl or $C_8$- to $C_{30}$-alkylene groups are straight-chain and branched alkyl or alkylene groups. Preference is given here to largely linear alkyl radicals, as occur in natural or synthetic fatty acids and fatty alcohols and also oxo alcohols, which optionally may be, additionally, mono- or di- or polyunsaturated. Examples thereof include n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene) etc.

The $C_5$- to $C_8$-cycloalkyl group is, for example, cyclopentyl, cyclohexyl, cycloheptyl or cyclooctyl.

In the text below, compounds which are derived from acrylic acid and methacrylic acid can sometimes be referred to in shortened form by adding the syllable "(meth)" to the compound derived from acrylic acid.

Component a)

Suitable compounds a) are, for example, the customary vinyl compounds known to the person skilled in the art which additionally have at least one group which is reactive toward isocyanate groups, which is preferably chosen from hydroxyl groups and also primary and secondary amino groups. Examples thereof include the esters of α,β-ethylenically unsaturated mono- and dicarboxylic acid with at least dihydric alcohols. α,β-Ethylenically unsaturated mono- and/or dicarboxylic acids which can be used are, for example, acrylic acid, methacrylic acid, fumaric acid, maleic acid, crotonic acid, itaconic acid, etc. and mixtures thereof. Suitable alcohols are customary diols, triols and polyols, e.g. 1,2-ethanediol, 1,3-propanediol, 1,4-butanediol, 1,5-pentanediol, 1,6-hexanediol, 1,10-decanediol, diethylene glycol, 2,2,4-trimethylpentane-1,5-diol, 2,2-dimethylpropane-1,3-diol, 1,4-dimethylolcyclohexane, 1,6-dimethylolcyclohexane, glycerol, trimethylolpropane, erythritol, pentaerythritol, sorbitol etc. The compounds a) are then, for example, hydroxymethyl (meth)acrylate, hydroxyethyl ethacrylate, 2-hydroxyethyl (meth)acrylate, 2-hydroxypropyl (meth)acrylate, 3-hydroxypropyl (meth)acrylate, 3-hydroxybutyl (meth)acrylate, 4-hydroxybutyl (meth)acrylate, 6-hydroxyhexyl (meth)acrylate, 3-hydroxy-2-ethylhexyl (meth)acrylate, and the di(meth)acrylates of 1,1,1-trimethylolpropane or of glycerol.

Suitable monomers a) are also the esters and amides of the abovementioned α,β-ethylenically unsaturated mono- and dicarboxylic acids with $C_2$- to $C_{12}$-aminoalcohols which have a primary or secondary amino group. These include aminoalkyl acrylates and aminoalkyl methacrylates and their N-monoalkyl derivatives which, for example, carry a N—$C_1$- to $C_8$-monoalkyl radical, such as aminomethyl (meth)acrylate, aminoethyl (meth)acrylate, N-methylaminomethyl (meth)acrylate, N-ethylaminomethyl (meth)acrylate, N-ethylaminoethyl (meth)acrylate, N-(n-propyl)aminomethyl (meth)acrylate, N-isopropylaminomethyl (meth)acrylate and preferably tert-butylaminoethyl acrylate and tert-butylaminoethyl methacrylate. Also included are N-(hydroxy-$C_1$–$C_{12}$-alkyl) (meth)acrylamides, such as N-hydroxymethyl(meth) acrylamide, N-hydroxyethyl(meth)acrylamide etc.

Suitable monomers a) are also the amides of the abovementioned α,β-ethylenically unsaturated mono- and dicarboxylic acids with di- or polyamines which have at least two primary or two secondary or one primary and one secondary amino group(s). Examples of these are the corresponding amides of acrylic acid and methacrylic acid, such as aminomethyl(meth)acrylamide, aminoethyl(meth) acrylamide, aminopropyl(meth)acrylamide, amino-n-butyl (meth)acrylamide, methylaminoethyl(meth)acrylamide, ethylaminoethyl(meth)acrylamide, methylaminopropyl (meth)acrylamide, ethylaminopropyl(meth)acrylamide, methylamino-n-butyl(meth)acrylamide etc.

Suitable monomers a) are also the reaction products of epoxy compounds which have at least one epoxy group with the abovementioned α,β-ethylenically unsaturated mono- and/or dicarboxylic acids and anhydrides thereof. Suitable epoxy compounds are, for example, glycidyl ethers, such as bisphenol-A diglycidyl ether, resorcinol diglycidyl ether, 1,3-propanediol diglycidyl ether, 1,4-butanediol diglycidyl ether, 1,5-pentanediol diglycidyl ether, 1,6-hexanediol diglycidyl ether etc.

Component b)

Component b) comprises customary aliphatic, cycloaliphatic and/or aromatic diisocyanates, such as tetramethylene diisocyanate, hexamethylene diisocyanate, methylenediphenyl diisocyanate, 2,4-and 2,6-toluylene diisocyanate and isomeric mixtures thereof, o-and m-xylylene diisocyanate, 1,5-naphthylene diisocyanate, 1,4-cyclohexylene diisocyanate, dicyclohexylmethane diisocyanate and mixtures thereof. Component b) preferably comprises hexamethylene diisocyanate, isophorone diisocyanate, o- and m-xylene diisocyanate, dicyclohexylmethane diisocyanate and mixtures thereof. If desired, up to 3 mol% of the specified compounds can be replaced by triisocyanates.

Component c)

Suitable compounds of component c) are, for example, diols, diamines, aminoalcohols, and mixtures thereof. The molecular weight of these compounds is preferably in a range from about 56 to 280. If desired, up to 3 mol% of the specified compounds can be replaced by triols or triamines.

Suitable diols c) are, for example, ethylene glycol, propylene glycol, butylene glycol, neopentyl glycol, cyclohexanedimethylol, di-, tri-, tetra-, penta- or hexaethylene glycol and mixtures thereof. Preference is given to using neopentyl glycol and/or cyclohexanedimethylol.

Suitable aminoalcohols c) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol, etc.

Suitable diamines c) are, for example, ethylenediamine, propylenediamine, 1,4-diaminobutane, 1,5-diaminopentane and 1,6-diaminohexane.

Preferred compounds of component c) are polymers having a number-average molecular weight in the range from about 300 to 5000, preferably about 400 to 4000, in particular 500 to 3000. Examples thereof include polyesterdiols, polyetherols, α,ω-diaminopolyethers and mixtures thereof. Preference is given to using ether-containing polymers.

The polyetherols c) are preferably polyalkylene glycols, e.g. polyethylene glycols, polypropylene glycols, polytetrahydrofurans etc., block copolymers of ethylene oxide and propylene oxide or block copolymers of ethylene oxide, propylene oxide and butylene oxide which comprise, in copolymerized form, the alkylene oxide units in random distribution or in the form of blocks.

Suitable α,ω-diaminopolyethers c) are, for example, obtainable by amination of polyalkylene oxides with ammonia.

Suitable polytetrahydrofurans c) can be obtained by cationic polymerization of tetrahydrofuran in the presence of acidic catalysts, such as, for example, sulfuric acid or fluorosulfuric acid. Such preparation processes are known to the person skilled in the art.

Polyesterdiols c) which can be used preferably have a number-average molecular weight in the range from about 400 to 5000, preferably 500 to 3000, in particular 600 to 2000.

Suitable polyesterdiols are all those which are customarily used for the preparation of polyurethanes, in particular those based on aromatic dicarboxylic acids, such as terephthalic acid, isophthalic acid, phthalic acid, Na- or K-sulfoisophthalic acid, etc., aliphatic dicarboxylic acids, such as adipic acid or succinic acid etc., and cycloaliphatic dicarboxylic acids, such as 1,2-, 1,3- or 1,4-cyclohexanedicarboxylic acid. Suitable diols are, in particular, aliphatic diols, such as ethylene glycol, propylene glycol, 1,6-hexanediol, neopentyl glycol, diethylene glycol, polyethylene glycols, polypropylene glycols, 1,4-dimethylolcyclohexane, and poly(meth)acrylate diols of the formula

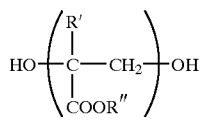

in which R' is H or $CH_3$, and R" is $C_1$–$C_{18}$-alkyl (in particular $C_1$–$C_{12}$- or $C_1$–$C_8$-alkyl), which have a molar mass of up to about 3000. Such diols can be prepared in the usual manner and are commercially available (Tegomer® products MD, BD and OD from Goldschmidt).

Preference is given to polyesterdiols based on aromatic and aliphatic dicarboxylic acids and aliphatic diols, in particular those in which the aromatic dicarboxylic acid constitutes from 10 to 95 mol%, in particular from 40 to 90 mol% and preferably from 50 to 85 mol%, of the total dicarboxylic acid content (remainder aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-$NaSO_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolcyclohexane and 5-$NaSO_3$-isophthalic acid/isophthalic acid/adipic acid/neopentyl glycol/diethylene glycol/dimethylolcyclohexane.

The compounds of component c) can be used individually or as mixtures.

Component d)

Component d) is preferably chosen from:

polysiloxanes of the formula I.1

$$Z^1—(CH_2)_a—\left[\begin{array}{c}R^1\\|\\Si—O\\|\\R^2\end{array}\right]_c \begin{array}{c}R^1\\|\\Si—(CH_2)_b—Z^2\\|\\R^2\end{array} \quad (I.1)$$

in which
a and b independently of one another are from 2 to 8,
c is from 3 to 100,
$R^1$ and $R^2$ independently of one another are $C_1$–$C_8$-alkyl, benzyl or phenyl,
$Z^1$ and $Z^2$ independently of one another are OH, $NHR^3$ or a radical of the formula II $$—O—(CH_2CH_2O)_v(CH_2CH(CH_3)O)_w—H \quad (II)$$

where
in formula II the order of the alkylene oxide units is arbitrary, and
v and w independently of one another are an integer from 0 to 200, the sum v+w being >0,
$R^3$ is hydrogen, $C_1$–$C_8$-alkyl or $C_5$–$C_8$-cycloalkyl;

polysiloxanes of the formula I.2

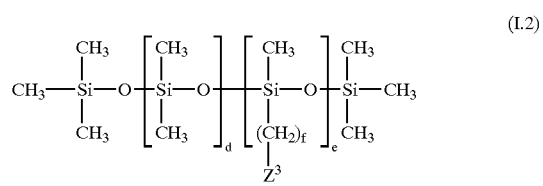

in which
the order of the siloxane units is arbitrary,
d and e independently of one another are from 0 to 100, the sum d+e being at least 2,
f is an integer from 2 to 8,
$Z^3$ is OH, $NHR^3$ or a radical of the formula II
where $R^3$ is hydrogen, $C_1$- to $C_8$-alkyl, $C_5$- to $C_8$-cycloalkyl or a radical of the formula —$(CH_2)_u$—$NH_2$, where u is an integer from 1 to 10, preferably from 2 to 6, polysiloxanes containing repeating units of the formula I.3

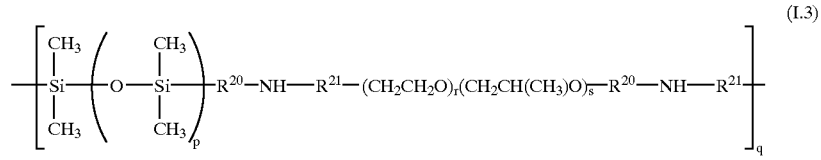

in which
p is an integer from 0 to 100,
q is an integer from 1 to 8,
$R^{20}$ and $R^{21}$ independently of one another are $C_1$- to $C_8$-alkylene,
the order of the alkylene oxide units is arbitrary and
r and s independently of one another are an integer from 0 to 200, the sum r+s being >0,
polysiloxanes of the formula I.4

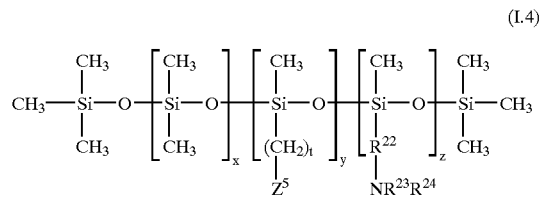

in which
$R^{22}$ is a $C_1$- to $C_8$-alkylene radical,
$R^{23}$ and $R^{24}$ independently of one another are hydrogen, $C_1$- to $C_8$-alkyl or $C_5$- to $C_8$-cycloalkyl,
the order of the siloxane units is arbitrary, x, y and z independently of one another are from 0 to 100, the sum x+y+z being at least 3, t is an integer from 2 to 8, $Z^5$ is a radical of the formula VII

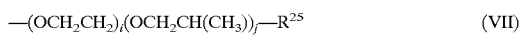

$$-(OCH_2CH_2)_i(OCH_2CH(CH_3))_j-R^{25} \qquad (VII)$$

in which
the order of the alkylene oxide units is arbitrary and i and j independently of one another are an integer from 0 to 200, the sum i+j being >0, $R^{25}$ is hydrogen or a $C_1$- to $C_8$-alkyl radical, and mixtures thereof.

In a suitable embodiment, the polysiloxanes d) of the formula I.1 do not have alkylene oxide radicals of the formula II. These polysiloxanes d) can preferably have a number-average molecular weight in the range from about 300 to 5000, preferably 400 to 3000.

Suitable polysiloxanes d) which do not have alkylene oxide radicals are, for example, the Tegomer® products from Goldschmidt.

In another suitable embodiment, the polysiloxanes d) are silicone-poly(alkylene oxide) copolymers of the formula I.1, at least one or both of the radicals $Z^1$ and/or $Z^2$ being a radical of the formula II.

Preferably, in formula II, the sum v+w is chosen such that the molecular weight of the polysiloxanes d) is then in a range from about 300 to 30,000.

Preferably, the total number of alkylene oxide units in the polysiloxanes d), i.e. the sum v+w in formula II is then in a range of from about 3 to 200, preferably 5 to 180.

In another suitable embodiment, the polysiloxanes d) are silicone-poly(alkylene oxide) copolymers of the formula I.2 which have at least one radical $Z^3$ of the formula II.

Preferably, in formula II, the sum v+w is then again chosen such that the molecular weight of the polysiloxanes d) is then in a range of from about 300 to 30,000. The total number of alkylene oxide units in the polysiloxanes d), i.e. the sum v+w in formula II, is then likewise preferably in a range of from about 3 to 200, preferably 5 to 180.

Suitable silicone-poly(alkylene oxide) copolymers d), which are known under the international nonproprietary name dimethicone, are the Tegopren® products from Goldschmidt, Belsil® 6031 from Wacker and Silvet® L from Witco.

In a preferred embodiment, the polysiloxanes d) are silicone-poly(alkylene oxide) copolymers of the formula I.2 which have at least one radical $Z^3$, in which $Z^3$ is $NHR^3$, and $R^3$ is hydrogen or a radical of the formula $-(CH_2)_u-NH_2$. u is preferably an integer from 1 to 10, preferably from 2 to 6. Examples thereof include the MAN and MAR products from Huls and the Finnish products from Wacker, e.g. Finnish WT 1270.

The polysiloxanes d) preferably include at least one compound of the formula I.3. In formula I.3, $R^{20}$ and $R^{21}$ independently of one another are preferably a $C_2$- to $C_4$-alkylene radical. In particular, $R^{20}$ and $R^{21}$ independently of one another are a $C_2$- to $C_3$-alkylene radical.

The molecular weight of the compound of the formula I.3 is preferably in the range of from about 300 to 100,000.

In formula I.3, p is preferably an integer of from 1 to 20, such as, for example, from 2 to 10.

The total number of alkylene oxide units in the compound of the formula I.3, i.e. the sum r+s, is preferably in a range of from about 3 to 200, preferably from 5 to 180.

Preferably, the end groups of the polysiloxanes with repeat units of the formula I.3 are chosen from $(CH_3)_3SiO$, H, $C_1$- to $C_8$-alkyl and mixtures thereof.

Amino-containing compounds with repeat units of the formula I.3 preferably have an amine number in a range of from about 2 to 50, in particular from 3 to 20.

Suitable alkoxylated siloxane amines of the formula I.3 are, for example, described in WO-A-97/32917, to the entire contents of which reference is made in this connection. Commercially available compounds are, for example, the Silsoft® products from Witco, e.g. Silsoft® A-843.

In formula I.4, the radical $R^{22}$ is preferably a $C_2$- to $C_4$-alkylene radical.

In formula I.4, $R^{23}$ and $R^{24}$ independently of one another are preferably hydrogen or $C_1$- to $C_4$-alkyl.

The sum x+y+z is preferably chosen such that the molecular weight of the compound of the formula I.4 is in a range of from about 300 to 100,000, preferably from 500 to 50,000.

The total number of alkylene oxide units in the radical of the formula VII, i.e. the sum of i+j, is preferably in a range of from about 3 to 200, preferably from 5 to 80.

In the formula VII, the radical $R^{25}$ is preferably hydrogen or $C_1$- to $C_4$-alkyl.

A suitable compound of the formula I.4 is, for example, Silsoft® A-858 from Witco.

Suitable polysiloxanes d) are also the polydimethylsiloxanes described in EP-A-277 816.

The urethane (meth)acrylates according to the invention preferably additionally comprise at least one component in incorporated form which is chosen from e) compounds which contain two or more active hydrogen atoms and at least one ionogenic and/or ionic group per molecule, f) monohydric alcohols, amines with a primary or secondary amino group, aliphatic, cycloaliphatic or aromatic monoisocyanates and mixtures thereof, g) α,β-ethylenically unsaturated compounds which additionally contain at least one isocyanate group per molecule, and mixtures thereof.

Component e)

The urethane (meth)acrylates according to the invention can additionally comprise, in copolymerized form, at least one component e) which contains at least one ionogenic and/or ionic group per molecule. These are preferably carboxylate groups and/or sulfonate groups or nitrogen-containing groups.

Suitable diamines and/or diols e) containing ionogenic or ionic groups are, for example, dimethylolpropanoic acid and compounds of the formula

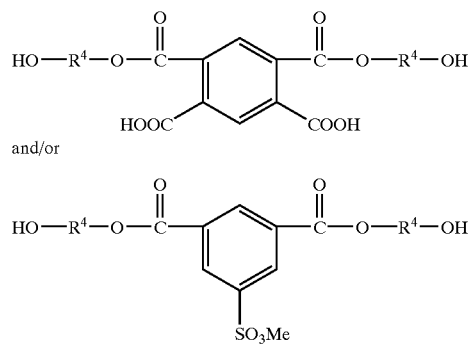

in which $R^4$ is in each case a $C_2-C_{18}$-alkylene group, and Me is Na or K.

Compounds which can be used as component e) are also those of the formula $$H_2N(CH_2)_n-NH-(CH_2)_m-COO^-M^+$$

and/or $$H_2N(CH_2)_n-NH-(CH_2)_m-SO_3^-M^+$$

in which m and n independently of one another are an integer of from 1 to 8, in particular from 1 to 6, and M is Li, Na or K.

When compounds containing nitrogen-containing groups are used as component e), cationic urethane (meth)acrylates are obtained. Components e) which can be used are, for example, compounds of the formulae $$HO-R^5-\underset{\underset{R^7}{|}}{N}-R^6-OH$$

$$R^8HN-R^5-\underset{\underset{R^7}{|}}{N}-R^6-NHR^9$$

$$HO-R^5-N\diagup\diagdown NH$$

$$R^8HN-R^5-N\diagup\diagdown NH$$

$$HO-R^5-N\diagup\diagdown N-R^6-OH$$

$$R^8HN-R^5-N\diagup\diagdown N-R^6-NHR^9$$

$$HO-R^5-\underset{\underset{R^{10}}{|}}{N^+}-R^6-OH \quad X^-$$

$$HO-R^5-\underset{\underset{X^-}{|}}{\overset{R^{10}}{N^+}}\diagup\diagdown \underset{\underset{R^{11}}{|}}{\overset{X^-}{N^+}}-R^6-OH$$

$$HO-R^5-\underset{\underset{R^7}{|}}{N^+}-R^6-OH \quad \text{with } (CH_2)_o-C(=O)-O^-$$

in which
R$^5$ and R$^6$, which can be identical or different, are C$_2$–C$_8$-alkylene,
R$^7$, R$^{10}$ and R$^{11}$, which can be identical or different, are C$_1$–C$_6$-alkyl, phenyl or phenyl-C$_1$–C$_4$-alkyl,
R$^8$ and R$^9$, which can be identical or different, are H or C$_1$–C$_6$-alkyl,
o is 1, 2 or 3,
X$^\ominus$ is chloride, bromide, iodide, C$_1$–C$_6$-alkylsulfate or SO$_4^{2-}$/$_2$.

Component f)

The urethane (meth)acrylates according to the invention can comprise, in incorporated form, a component f) which is chosen from monohydric alcohols, amines with a primary or secondary amino group, aliphatic, cycloaliphatic or aromatic monoisocyanates and mixtures thereof. Preferred compounds f) are generally compounds of the formula R$^{12}$—Z$^4$, in which R$^{12}$ is a C$_2$- to C$_{30}$-alkyl radical, and Z$^4$ has the meanings given in formula I.1 for Z$^1$ and Z$^2$ or is NCO.

Suitable monohydric alcohols f) have a straight-chain or branched alkyl radical having from 2 to 30 carbon atoms, preferably from 8 to 22 carbon atoms, which optionally can be additionally mono-, di- or polyunsaturated. Suitable C$_2$- to C$_{30}$-alkyl radicals are those mentioned above. The alcohols f) can be used individually or as mixtures.

Preferred monohydric alcohols f) are, for example, ethanol, n-propanol, nonanol, undecanol, tridecanol, tetradecanol, pentadecanol, hexadecanol, heptadecanol, octadecanol, etc. and mixtures thereof. The alcohols can be used in this connection as pure isomers or in the form of isomeric mixtures.

Preferred hydroxyl-containing compounds f) are furthermore the alkoxylates of the abovementioned C$_2$- to C$_{30}$-alkanols of the formula III $$R^{12}-(CH_2CH_2O)_g(CH_2CH(CH_3)O)_h-H \quad \text{(III)}$$

where, in the formula III, the order of the alkylene oxide units is arbitrary, g and h independently of one another are an integer from 0 to 200, the sum g+h being >0, and R$^{12}$ is as defined above.

Suitable higher primary or secondary amines f) are amines and amine mixtures which have one or two of the abovementioned C$_1$- to C$_{30}$-alkyl radicals. These can be obtained, for example, by reaction of natural or synthetic fatty acids or fatty acid mixtures with ammonia to give nitriles and subsequent hydrogenation. Examples thereof include alkylamines which have the alkyl radicals specified above for the monohydric alcohols f), i.e. ethyl- and the isomeric propyl-, butyl-, pentyl-, hexyl-, heptyl-, octyl-, nonyl-, decyl-, undecyl-, dodecyl-, tridecyl-, tetradecyl-, pentadecyl-, hexadecyl-, heptadecyl-, octadecylamines etc. and mixtures thereof.

Examples of suitable monoisocyanates f) are C$_1$- to C$_{30}$-alkyl isocyanates, which are obtainable from the abovementioned amines and amine mixtures by phosgenation or from natural or synthetic fatty acids and fatty acid mixtures by Hofmann, Curtius or Lossen degradation.

Suitable cycloaliphatic monoisocyanates f) are, for example, cyclohexyl isocyanate, 2-, 3- and 4-methylcyclohexyl isocyanate, etc. and mixtures thereof.

Suitable aromatic monoisocyanates f) are, for example, phenyl isocyanate, 2-, 3- and 4-methylphenyl isocyanate, etc. and mixtures thereof.

Component g)

Component g) comprises, for example, isocyanates of the formula $$CHR^{13}=CH-\underset{}{\text{C}_6\text{H}_4}-C(CH_3)_2-NCO \quad \text{(IV)}$$

in which
the —C(CH$_3$)$_2$—NCO group can be in the o-, m- or p-position relative to the vinyl group, and R$^{13}$ is hydrogen or C$_1$- to C$_8$-alkyl.

Preferably, in formula IV, R$^{13}$ is hydrogen, methyl or ethyl.

In a first possible embodiment, the urethane (meth) acrylates according to the invention are nonionic compounds. These then comprise none of the abovementioned compounds e) in incorporated form.

In a second possible embodiment, the urethane (meth) acrylates according to the invention are ionic compounds. These then have at least one ionic or ionogenic group, i.e. they comprise, in incorporated form, at least one of the abovementioned compounds of component e). If these compounds e) have, as ionogenic or ionic group, at least one carboxylate group and at least one sulfonate group, then anionic urethane (meth)acrylates result. Preferably, for the preparation of these anionic compounds, dimethylolpropanoic acid is used as compound e). If the compound of component e) is a compound containing a nitrogen-containing group, then cationic urethane (meth)acrylates result. A preferred compound e) for the preparation of cationic urethane (meth)acrylates is N-methyldipropylenetriamine.

The urethane (meth)acrylates according to the invention are prepared by reacting at least one diisocyanate b) and optionally one or more isocyanate-containing compounds f) and/or g) with the groups of the other components a), c), d) and optionally e) and/or f) that are reactive toward isocyanate groups. If hydroxyl-containing components are used for the reaction with the isocyanate-containing components, then the total amount of isocyanate is preferably reacted with the hydroxyl-containing components to give an isocyanate-containing polyurethane prepolymer. This reaction is generally carried out at elevated temperature in the range from about 40 to 150° C., preferably from about 50 to 100° C. The reaction can be carried out without solvent in the melt or in a suitable solvent or solvent mixture. These include ketones, such as acetone and methyl ethyl ketone. In the reaction of the isocyanate-containing compounds of components b), f) and/or g) with the hydroxyl-containing compounds of components a), c), d) and e) and/or f), the ratio of NCO equivalent in the compounds of components b), f) and/or g) to equivalent of active hydrogen atom in the other components is chosen such that a polyurethane prepolymer results which still has free isocyanate groups. In general, the ratio of NCO equivalent to equivalent of active hydrogen atom of the hydroxyl-containing compounds is >1:1 to 1.3:1, preferably 1.05:1 to 1.2:1. The subsequent reaction of the isocyanate-containing polyurethane prepolymer to give the urethane (meth)acrylate according to the invention is preferably likewise carried out in one of the abovementioned solvents. If desired, the reaction can, however, be carried out without a solvent. The temperature is generally in the range of from about 0 to 60° C., preferably about 10 to 50° C. The amine-containing components a), c), d), e) and/or f) are generally used in an amount such that the free isocyanate groups of the polyurethane prepolymer are at least partially, but preferably completely reacted. Where necessary, isocyanate groups which are present are finally deactivated by addition of alcohols, e.g. ethanol, amines, e.g. 2-amino-2-methyl-1-propanol, or mixtures thereof.

The urethane (meth)acrylates which do not comprise, in incorporated form, hydroxyl-containing components are prepared by reacting the amine-containing components with the isocyanate-containing components at a temperature in the range from about 0 to 60° C. In this connection, either the isocyanate components, or the amine-containing components can be initially introduced for the reaction. Suitable solvents for this reaction are, for example, water, $C_1$–$C_4$-alcohols, such as methanol, n-propanol, isopropanol, n-butanol and, preferably, ethanol and the abovementioned ketones.

The invention further relates to a process for the preparation of a urethane (meth)acrylate having urea groups, where components a), c) and d) and optionally e) and/or f) are used, the active hydrogen atoms of which are essentially in the form of primary and/or secondary amino groups, and these are reacted with at least one isocyanate-containing component b) and optionally f) and/or g) in a solvent chosen from water, $C_1$- to $C_4$-alkanols and mixtures thereof.

Preferably, in the process according to the invention, the content of hydroxyl-containing components a), c), d), e) and/or f), based on the total amount of these components, is from 0 to 10% by weight, preferably from 0 to 5% by weight, in particular from 0.01 to 1% by weight.

The solvents used in the process according to the invention are generally advantageously also suitable for the copolymerization of the urethane (meth)acrylates, described below, for the preparation of water-soluble or water-dispersible polymers. It is thus generally possible to avoid exchanging the solvent. The solvents used in the process according to the invention are generally also advantageously suitable for the preparation of formulations of these water-soluble or water-dispersible polymers.

Urethane (meth)acrylates which contain acid groups can be converted into a water-soluble or water-dispersible form by partial or complete neutralization with a base, and those containing amino groups can be converted by neutralization with an acid or by quaternization. Generally, the resulting salts of the urethane (meth)acrylates have better solubility in water or dispersibility in water than the unneutralized form. Suitable bases for the neutralization of acid-containing urethane (meth)acrylates and acids or quaternizing agents for the protonation or quaternization of amine-containing urethane (meth)acrylates are given below for the neutralization or quaternization of the polymers based on the urethane (meth)acrylates according to the invention.

If desired, it is also possible to use the urethane (meth) acrylates according to the invention in unneutralized or nonquaternized form for the reaction with free-radically polymerizable compounds, as described below.

The invention further relates to the use of the above-described, free-radically polymerizable, siloxane-containing urethane (meth)acrylates as component for the preparation of polymers. This permits the preparation of siloxane-containing polymers by free-radical copolymerization of the urethane (meth)acrylates with at least one other compound which likewise has at least one free-radically polymerizable α,β-ethylenically unsaturated double bond. This other component can be at least one free-radically polymerizable monomer, oligomer and/or polymer and mixtures thereof.

The invention further relates to a water-soluble or water-dispersible polymer which comprises, in copolymerized form, at least one urethane (meth)acrylate according to the invention and at least one free-radically polymerizable α,β-ethylenically unsaturated monomer M).

The water-soluble or water-dispersible polymers according to the invention generally comprise the urethane (meth) acrylates in an amount of from about 0.05 to 80% by weight, preferably from 0.1 to 50% by weight, in particular from 0.5 to 35% by weight, based on the total amount of urethane (meth)acrylate and monomer M).

The monomer M) is preferably chosen from

M1) essential hydrophobic, nonionic compounds, preferably esters of α,β-ethylenically unsaturated mono- and/or dicarboxylic acids with $C_1$–$C_{30}$-alkanols, amides of α,β-ethylenically unsaturated mono- and/or dicarboxylic acids with mono- and di-$C_1$–$C_{30}$-alkylamines, esters of vinyl alcohol or allyl alcohol with $C_1$–$C_{30}$-monocarboxylic acids, vinyl ethers, vinyl aromatics, vinyl halides, vinylidene halides, $C_2$–$C_8$-monoolefins, nonaromatic hydrocarbons having at least 2 conjugated double bonds and mixtures thereof, M2) compounds containing a free-radically polymerizable α,β-ethylenically unsaturated double bond and at least one ionogenic and/or ionic group per molecule, M3) essentially hydrophilic, nonionic compounds, preferably N-vinylamides, N-vinyllactams, primary amides of α,β-ethylenically unsaturated monocarboxylic acids, vinyl- and allyl-substituted heteroaromatic compounds, esters of α,β-ethylenically unsaturated mono- and dicarboxylic acids with $C_1$–$C_{30}$-alkanediols, esters and amides of α,β-ethylenically unsaturated mono- and dicarboxylic acids with $C_2$–$C_{30}$-amino alcohols which have a primary or secondary amino group, polyether acrylates, and mixtures thereof, and mixtures thereof.

Suitable monomers M1) are essentially hydrophobic, nonionic monomers. Examples thereof include vinyl formate, vinyl acetate, vinyl propionate, vinyl n-butyrate, vinyl stearate, vinyl laurate, styrene, α-methylstyrene, o-chlorostyrene, vinyltoluenes, vinyl chloride, vinylidene chloride, ethylene, propylene, butadiene, isoprene, chloroprene, methyl vinyl ether, ethyl vinyl ether, butyl vinyl ether, dodecyl vinyl ether etc.

Examples of preferred monomers M1) are the esters of α,β-ethylenically unsaturated mono- and dicarboxylic acids with $C_1$–$C_{30}$-alkanols, preferably $C_1$–$C_{22}$-alkanols. Preference is also given to the amides of α,β-ethylenically unsaturated mono- and dicarboxylic acids with mono- and dialkylamines which have from 1 to 30 carbon atoms, preferably from 1 to 22 carbon atoms, per alkyl radical. These compounds are preferably of the formula V

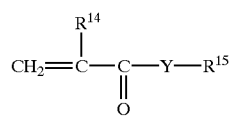

(V)

in which $R^{14}$ is hydrogen or $C_1$- to $C_8$-alkyl, $R^{15}$ is a straight-chain or branched $C_1$- to $C_{30}$-alkyl radical, and Y is O or $NR^{16}$, where $R^{16}$ is hydrogen, $C_1$- to $C_8$-alkyl or $C_5$- to $C_8$-cycloalkyl.

Preferably, in formula V, $R^{14}$ is hydrogen, methyl or ethyl. Y is preferably O or NH.

Suitable radicals $R^{15}$ are the abovementioned $C_1$–$C_{30}$-alkyl radicals. In particular, $R^{15}$ is methyl, ethyl, n-propyl, isopropyl, n-butyl, 2-butyl, sec-butyl, tert-butyl, n-pentyl, n-hexyl, n-heptyl, n-octyl, ethylhexyl, 1,1,3,3-tetramethylbutyl, undecyl, lauryl, tridecyl, myristyl, pentadecyl, palmityl, margarinyl, stearyl, palmitoleinyl, oleyl or linoyl.

In particular, the monomer M1) is chosen from methyl (meth)acrylate, methyl ethacrylate, ethyl (meth)acrylate, ethyl ethacrylate, tert-butyl (meth)acrylate, tert-butyl ethacrylate, n-octyl (meth)acrylate, 1,1,3,3-tetramethylbutyl (meth)acrylate, ethylhexyl (meth)acrylate, n-nonyl (meth) acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth) acrylate, nonadecyl (meth)acrylate, arrachinyl (meth) acrylate, behenyl (meth)acrylate, lignocerenyl (meth) acrylate, cerotinyl (meth)acrylate, melissinyl (meth) acrylate, palmitoleinyl (meth)acrylate, oleyl (meth)acrylate, linolyl (meth)acrylate, linolenyl (meth)acrylate, stearyl (meth)acrylate, lauryl (meth)acrylate, tert-butyl(meth) acrylamide, n-octyl(meth)acrylamide, 1,1,3,3-tetramethylbutyl(meth)acrylamide, ethylhexyl(meth) acrylamide, n-nonyl(meth)acrylamide, n-decyl(meth) acrylamide, n-undecyl(meth)acrylamide, tridecyl(meth) acrylamide, myristyl(meth)acrylamide, pentadecyl(meth) acrylamide, palmityl(meth)acrylamide, heptadecyl(meth) acrylamide, nonadecyl(meth)acrylamide, arrachinyl(meth) acrylamide, behenyl(meth)acrylamide, lignocerenyl(meth) acrylamide, cerotinyl(meth)acrylamide, melissinyl(meth) acrylamide, palmitoleinyl(meth)acrylamide, oleyl(meth) acrylamide, linolyl(meth)acrylamide, linolenyl(meth) acrylamide, stearyl(meth)acrylamide, lauryl(meth) acrylamide and mixtures thereof.

Preferred monomers M1) are the esters of α,β-ethylenically unsaturated mono- and dicarboxylic acids with straight-chain and/or branched $C_1$–$C_6$-alkanols, preferably $C_2$–$C_4$-alkanols, e.g. the esters of acrylic acid and/or methacrylic acid with methanol, ethanol, n-propanol, isopropanol, n-butanol, sec-butanol, tert-butanol, n-pentanol, 2-methylbutanol, n-hexanol, etc.

Preferred monomers M1) are also amides of α,β-ethylenically unsaturated mono- and dicarboxylic acids with mono- and dialkylamines having straight-chain and/or branched alkyl radicals which have from 1 to 6 carbon atoms, preferably from 2 to 4 carbon atoms per alkyl radical. Examples thereof include N—$C_1$- to $C_6$-alkyl(meth) acrylamide, such as N-methyl(meth)acrylamide, N-ethyl (meth)acrylamide, N-(n-propyl)(meth)acrylamide, N-isopropyl(meth)acrylamide, N-(n-butyl)(meth) acrylamide, N-(tert-butyl)(meth)acrylamide, N-(n-pentyl) (meth)acrylamide, N-(n-hexyl)(meth)acrylamide, N,N-dimethyl(meth)acrylamide, N,N-diethyl(meth)acrylamide etc.

Preferably, component M1) includes at least one ester of an α,β-ethylenically unsaturated mono- and/or dicarboxylic acid with a linear $C_2$- to $C_6$-alkanol. In particular, it is an ester of acrylic acid and/or methacrylic acid with ethanol, n-propanol, n-butanol, n-pentanol and n-hexanol. Specifically, component M1) includes n-butyl acrylate and/or n-butyl methacrylate.

Component M1) preferably includes at least one ester of an α,β-ethylenically unsaturated mono- and/or dicarboxylic acid with a branched $C_2$–$C_6$-alkanol. Specifically, component M1) includes tert-butyl acrylate and/or tert-butyl methacrylate.

Component M1) preferably includes at least one linear $C_1$- to $C_6$-alkyl (meth)acrylate and/or -acrylamide, in particular n-butyl (meth)acrylate and/or n-butyl(meth) acrylamide.

Component M1) preferably includes at least one branched $C_1$- to $C_6$-alkyl (meth)acrylate and/or -acrylamide, in particular tert-butyl (meth)acrylate and/or tert-butyl(meth) acrylamide.

Particular preference is given to using, as component M1), a monomer mixture which comprises at least one of the abovementioned linear $C_1$- to $C_6$-alkyl (meth)acrylates and/or -acrylamides and at least one of the abovementioned branched $C_1$- to $C_6$-alkyl (meth)acrylates and/or -acrylamides.

The compounds M2) have at least one ionogenic or ionic group per molecule which is preferably chosen from carboxylate groups and/or sulfonate groups and salts thereof obtainable by partial or complete neutralization with a base, and also tertiary amine groups, which can be partially or completely protonated and quaternized. Suitable bases for the neutralization, or acids for the protonation, and alkylating agents for the quaternization are those given above.

Suitable monomers M2) are, for example, the abovementioned α,β-ethylenically unsaturated mono- and/or dicarboxylic acids and the half-esters and anhydrides thereof, such as acrylic acid, methacrylic acid, fumaric acid, maleic acid, itaconic acid, crotonic acid, maleic anhydride, monobutyl maleate etc. Preference is given to using acrylic acid, methacrylic acid and the alkali metal salts thereof, such as the sodium and potassium salts thereof.

Suitable monomers M2) are also acrylamidoalkanesulfonic acids and salts thereof, such as 2-acrylamido-2-methylpropanesulfonic acid and the alkali metal salts thereof, e.g. the sodium and potassium salts thereof.

Other suitable compounds M2) are the esters of the abovementioned α,β-ethylenically unsaturated mono- and dicarboxylic acids with $C_2$- to $C_{12}$-aminoalcohols which are $C_1$- to $C_8$-dialkylated on the amine nitrogen. Examples thereof include N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminocyclohexyl (meth)acrylate etc. Preference is given to using N,N-dimethylaminopropyl acrylate and N,N-dimethylaminopropyl (meth)acrylate.

Suitable monomers M2) are also the amides of the abovementioned α,β-ethylenically unsaturated mono- and dicarboxylic acids with diamines which have a tertiary and a primary or secondary amino group. Examples thereof include N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)-butyl]methacrylamide, N-[2-(diethylamino)ethyl]acrylamide, N-[4-(dimethylamino)cyclohexyl]acrylamide, N-[4-(dimethylamino)cyclohexyl]methacrylamide etc.

Suitable monomers M3) are essentially hydrophilic, nonionic monomers. Examples thereof include N-vinylamides, such as N-vinylformamide, N-vinylacetamide, N-vinylpropionamide etc. Preference is given to using N-vinylformamide.

Suitable monomers M3) are also N-vinyllactams and their derivatives, which can, for example, have one or more $C_1$–$C_6$-alkyl substituents, such as methyl, ethyl, n-propyl, isopropyl, n-butyl, sec-butyl, tert-butyl etc. Examples thereof include N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc.

Suitable monomers M3) are also primary amides of the abovementioned α,β-ethylenically unsaturated monocarboxylic acids, such as acrylamide, methacrylamide, ethacrylamide etc.

Suitable monomers M3) are also vinyl- and allyl-substituted heteroaromatic compounds, such as 2- and 4-vinylpyridine, -allylpyridine, and preferably N-vinyl heteroaromatics, such as N-vinylimidazole, N-vinyl-2-methylimidazole etc.

Suitable monomers M3) are also the esters of α,β-ethylenically unsaturated mono- and dicarboxylic acid, such as acrylic acid, methacrylic acid, fumaric acid, maleic acid, itaconic acid, crotonic acid etc., with $C_1$–$C_{30}$-alkanediols. Examples thereof include 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate etc. Preference is given to using hydroxyethyl acrylate and hydroxyethyl methacrylate. Suitable monomers e) are also the esters of the abovementioned acids with triols and polyols, such as, for example, glycerol, erythritol, pentaerythritol, sorbitol etc.

Suitable compounds M3) are also polyether acrylates of the formula VI

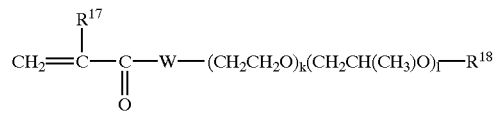

(VI)

in which
the order of the alkylene oxide units is arbitrary, k and l, independently of one another are an integer from 0 to 50, the sum k+l being at least 5,
$R^{17}$ is hydrogen or $C_1$- to $C_8$-alkyl, and
$R^{18}$ is hydrogen or $C_1$- to $C_6$-alkyl,
W is O or $NR^{19}$, where $R^{19}$ is hydrogen, $C_1$- to $C_8$-alkyl or $C_5$- to $C_8$-cycloalkyl.

The polyether acrylates M3) are preferably compounds of the formula VI in which the sum k+l is an integer from 5 to 70, preferably from 6 to 50.

In formula VI, $R^{17}$ is preferably hydrogen, methyl, ethyl, n-propyl, isopropyl, n-butyl, sec-butyl, tert-butyl, n-pentyl or n-hexyl, in particular hydrogen, methyl or ethyl.

$R^{18}$ in the formula VI is preferably hydrogen, methyl, ethyl, n-propyl, isopropyl, n-butyl, sec-butyl, n-pentyl or n-hexyl.

W in formula VI is preferably O or NH.

Suitable polyether acrylates M3) are, for example, the polycondensation products of the abovementioned α,β-ethylenically unsaturated mono- and/or dicarboxylic acids and their acid chlorides, amides and anhydrides with polyetherols. Suitable polyetherols can be readily prepared by reaction of ethylene oxide, 1,2-propylene oxide and/or epichlorohydrin with a starter molecule, such as water or a short-chain alcohol $R^{16}$—OH. The alkylene oxides can be used individually, alternately one after the other or as a mixture. The polyether acrylates M3) can be used alone or in mixtures for the preparation of the polymers used according to the invention.

In a first preferred embodiment, the water-soluble or water-dispersible polymers according to the invention comprise at least one urethane (meth)acrylate according to the invention as described above, at least one essentially hydrophobic, nonionic compound M1) and at least one ionogenic or ionic compound M2) in incorporated form. Where appropriate, these polymers can additionally comprise, in copolymerized form, at least one other compound of component M3).

The polymer preferably comprises, in copolymerized form,
from 0.1 to 50% by weight, preferably from 0.5 to 35% by weight, of at least one urethane (meth)acrylate according to the invention,
from 40 to 75% by weight, preferably from 45 to 73% by weight, of at least one component M1),
from 10 to 35% by weight, preferably from 18 to 30% by weight, of at least one component M2), from 0 to 30% by weight of at least one component M3).

Particular preference is given to polymers which comprise, in copolymerized form,

- from 0.1 to 50% by weight, preferably from 0.5 to 35% by weight, of at least one urethane (meth)acrylate according to the invention,
- from 40 to 75% by weight, preferably from 45 to 73% by weight, of at least one component M1) which is chosen from linear and branched $C_1$- to $C_6$-alkyl (meth) acrylates, $C_1$- to $C_6$-alkyl (meth)acrylamides and mixtures thereof,
- from 10 to 35% by weight, preferably from 18 to 30% by weight, of at least one $\alpha,\beta$-ethylenically unsaturated mono- and/or dicarboxylic acid M2), preferably acrylic acid, methacrylic acid and mixtures thereof,
- from 0 to 30% by weight, preferably from 0.1 to 25% by weight, of at least one component M3).

Particular preference is also given to polymers which comprise, in copolymerized form,

- from 0.1 to 50% by weight, preferably from 0.5 to 35% by weight, of at least one urethane (meth)acrylate according to the invention,
- from 40 to 75% by weight, preferably from 45 to 73% by weight, of at least one component M1) which is chosen from linear and branched $C_1$- to $C_6$-alkyl (meth) acrylates, $C_1$- to $C_6$-alkyl (meth)acrylamides and mixtures thereof,
- from 10 to 35% by weight, preferably from 18 to 30% by weight, of at least one component M2) which is chosen from esters of the abovementioned $\alpha,\beta$-ethylenically unsaturated mono- and dicarboxylic acids with $C_2$- to $C_{12}$-aminoalcohols which are $C_1$- to $C_8$-dialkylated on the amine nitrogen, amides of the abovementioned $\alpha,\beta$-ethylenically unsaturated mono- and dicarboxylic acids with diamines which have a tertiary and a primary or secondary amino group, and mixtures thereof,
- from 0 to 30% by weight, preferably from 0.1 to 25% by weight, of at least one component M3).

In another preferred embodiment, the water-soluble or water-dispersible polymers according to the invention comprise, in incorporated form, at least one urethane (meth) acrylate according to the invention as described above and at least one essentially hydrophilic, nonionic compound M3). Where appropriate, these polymers can additionally comprise, in copolymerized form, at least one other compound chosen from the compounds of components M1) and/or M2).

The polymer preferably comprises, in copolymerized form,

- from 0.1 to 50% by weight, preferably from 0.5 to 35% by weight, of at least one urethane (meth)acrylate according to the invention,
- from 0 to 50% by weight of at least one component M1),
- from 0 to 20% by weight, of at least one component M2),
- 25 from to 80% by weight of at least one component M3).

Particular preference is given to polymers which comprise, in copolymerized form,

- from 0.1 to 50% by weight, preferably from 0.5 to 35% by weight, of at least one urethane (meth)acrylate according to the invention,
- from 0 to 50% by weight, preferably from 0.1 to 45% by weight, of at least one component M1) chosen from linear and branched $C_1$- to $C_6$-alkyl (meth)acrylates, $C_1$- to $C_6$-alkyl(meth)acrylamides and mixtures thereof,
- from 0 to 20% by weight, preferably from 0.1 to 18% by weight, of at least one component M2) which is chosen from esters of the abovementioned $\alpha,\beta$-ethylenically unsaturated mono- and dicarboxylic acids with $C_2$- to $C_{12}$-aminoalcohols which are $C_1$- to $C_8$-dialkylated on the amine nitrogen, amides of the abovementioned $\alpha,\beta$-ethylenically unsaturated mono- and dicarboxylic acids with diamines which have a tertiary and a primary or secondary amino group, and mixtures thereof,
- from 25 to 80% by weight of at least one component M3) chosen from N-vinyllactams and derivatives thereof, preferably N-vinylpyrrolidone and/or N-vinylcaprolactam.

The polymers preferably comprise, in copolymerized form and as component M1), at least one linear $C_1$- to $C_6$-alkyl (meth)acrylate and/or -acrylamide, in particular n-butyl (meth)acrylate and/or n-butyl(meth)acrylamide, and at least one branched $C_1$- to $C_6$-alkyl (meth)acrylate and/or -acrylamide, in particular tert-butyl (meth)acrylate and/or tert-butyl(meth)acrylamide.

The polymers according to the invention preferably have, as component M2), at least one compound containing at least one anionogenic and/or anionic group per molecule. The acid number of these polymers is then preferably in a range from 30 to 190 mg of KOH/g.

The polymers according to the invention preferably have, as component M2), at least one compound containing at least one cationogenic and/or cationic group per molecule. The amine number or the quaternary ammonium number of the polymers according to the invention is then preferably in a range from about 30 to 190 mg of KOH/g.

The polymers according to the invention are prepared by free-radical polymerization by customary processes known to the person skilled in the art. These include free-radical bulk, emulsion, suspension and solution polymerization, preferably emulsion and solution polymerization. The amounts of compounds to be polymerized, based on solvents and dispersants, are generally chosen here such that about 30 to 80% by weight solutions, emulsions or dispersions are obtained. The polymerization temperature is generally from 30 to 120° C., preferably from 40 to 100° C. The polymerization medium for the solution polymerization can consist either of only one organic solvent or of mixtures of water and at least one water-miscible, organic solvent. Preferred organic solvents are, for example, alcohols, such as methanol, ethanol, n-propanol, isopropanol, n-butanol, ketones, such as acetone and methyl ethyl ketone, tetrahydrofuran etc. The solution polymerization can be carried out either as a batch process or in the form of a feed process, including monomer feed, staged and gradient procedures. Preference is generally given to the feed process, in which, if desired, some of the polymerization mixture is introduced as an initial charge and heated to the polymerization temperature, and then the remainder of the polymerization mixture, usually by way of one or more spatially separate feeds, is supplied to the polymerization zone continuously, in stages or under a concentration gradient, while the polymerization is maintained.

The initiators for the free-radical polymerization are customary peroxo or azo compounds. Examples thereof include dibenzoyl peroxide, tert-butyl perpivalate, tert-butyl per-2-ethylhexanoate, di-tert-butyl peroxide, 2,5-dimethyl-2,5-di (tert-butylperoxy)hexane, aliphatic or cycloaliphatic azo compounds, e.g. 2,2'-azobis(isobutyronitrile), 2,2'-azobis(2-methylbutyronitrile), 2,2'-azobis(2,4-dimethylvaleronitrile), 1,1'-azobis(1-cyclohexanecarbonitrile), 2-(carbamoylazo) isobutyronitrile, 4,4'-azobis(4-cyanovaleric acid) and the alkali metal and ammonium salts thereof, e.g. the sodium salt, dimethyl 2,2'-azobisisobutyrate, 2,2'-azobis[2-(2-imidazolin-2-yl)propane], 2,2'-azobis(2-amidinopropane) and the acid addition salts of the latter two compounds, e.g., the dihydrochlorides.

Also suitable as initiators are hydrogen peroxide, hydroperoxides in combination with reducing agents, and persalts. Suitable hydroperoxides are, for example, t-butyl hydroperoxide, t-amyl hydroperoxide, cumene hydroperoxide and pinane hydroperoxide, in each case in combination with, for example, a salt of hydroxymethanesulfinic acid, an iron(II) salt or ascorbic acid. Suitable persalts are, in particular, alkali metal peroxodisulfates.

The amount of initiator used, based on the monomers, is generally in a range of from about 0.1 to 2% by weight, based on the total weight of the monomers to be polymerized.

The K values of the resulting copolymers are preferably in a range of from about 15 to 90, preferably from 20 to 70, in particular from 25 to 60 (1% strength by weight solution in ethanol). To achieve the desired K value it is possible, particularly in the case of emulsion or suspension polymerization, to use a regulator. Suitable regulators are, for example, aldehydes, such as formaldehyde, acetaldehyde, propionaldehyde, n-butyraldehyde and isobutyraldehyde, formic acid, ammonium formate, hydroxylammonium sulfate and hydroxylammonium phosphate. It is also possible to use regulators which contain sulfur in organically bonded form, such as di-n-butyl sulfide, di-n-octyl sulfide, diphenyl sulfide etc., or regulators which contain sulfur in the form of SH groups, such as n-butyl mercaptan, n-hexyl mercaptan or n-dodecyl mercaptan. Also suitable are water-soluble, sulfur-containing polymerization regulators, such as, for example, hydrogen sulfites and disulfites. Further suitable regulators are allyl compounds, such as allyl alcohol or allyl bromide, benzyl compounds, such as benzyl chloride or alkyl halides, such as chloroform or tetrachloromethane.

If desired, following the polymerization reaction, one or more polymerization initiators are added to the polymer solution, and the polymer solution is heated, for example to the polymerization temperature or to temperatures above the polymerization temperature in order to complete the polymerization. Suitable initiators are the azo initiators mentioned above, and also all other customary initiators suitable for free-radical polymerization in aqueous solution, for example peroxides, hydroperoxides, peroxodisulfates, percarbonates, peroxo esters and hydrogen peroxide. These take the polymerization reaction to a higher conversion, such as, for example, 99.9%. The solutions forming in the polymerization can, where appropriate, be converted into solid powders by a prior art drying technique. Preferred techniques are, for example, spray drying, spray fluidized-bed drying, roller drying and belt drying. Freeze drying and freeze concentration can likewise be used. If desired, the solvent can also be removed, partially or completely, by customary methods, e.g. distillation under reduced pressure.

In a suitable embodiment, the polymers according to the invention are nonionic polymers.

In another suitable embodiment, the water-soluble or water-dispersible polymers according to the invention are anionic or anionogenic polymers. The acid groups of the polymers can be partially or completely neutralized with a base. Generally, the resulting salts of the polymers have better solubility or dispersibility in water than the nonneutralized polymers. Bases which can be used for neutralization of the polymers are alkali metal bases such as sodium hydroxide solution, potassium hydroxide solution, sodium carbonate, sodium hydrogencarbonate, potassium carbonate or potassium hydrogencarbonate, and alkaline earth metal bases such as calcium hydroxide, calcium oxide, magnesium hydroxide or magnesium carbonate, and ammonia and amines. Examples of suitable amines are $C_1$–$C_6$-alkylamines, preferably n-propylamine and n-butylamine, dialkylamines, preferably diethylpropylamine and dipropylmethylamine, trialkylamines, preferably triethylamine and triisopropylamine, $C_1$–$C_6$-alkyldiethanolamines, preferably methyl- or ethyldiethanolamine and di-$C_1$–$C_6$-alkylethanolamines. Particularly for use in hair-treatment compositions, 2-amino-2-methyl-1-propanol, 2-amino-2-ethylpropane-1,3-diol, diethylaminopropylamine and triisopropanolamine have proven successful for the neutralization of the polymers containing acid groups. The neutralization of the polymers containing acid groups can also be carried out using mixtures of two or more bases, e.g. mixtures of sodium hydroxide solution and triisopropanolamine. Depending on the intended use, the neutralization can be carried out partially, e.g. to from 5 to 95%, preferably from 30 to 95%, or completely, i.e. to 100%.

In another suitable embodiment, the water-soluble or water-dispersible polymers according to the invention are cationic or cationogenic polymers. Because of their cationic groups, the polymers containing amine groups or protonated or quaternized amine groups are generally readily soluble in water or water/alcohol mixtures, or are at least dispersible without the assistance of emulsifiers. Charged cationic groups can be produced from the tertiary amine nitrogens present either by protonation, e.g. with carboxylic acids, such as lactic acid, or mineral acids, such as phosphoric acid, sulfuric acid and hydrochloric acid, or by quaternization, e.g. with alkylating agents, such as $C_1$- to $C_4$-alkyl halides or sulfates. Examples of such alkylating agents are ethyl chloride, ethyl bromide, methyl chloride, methyl bromide, dimethyl sulfate and diethyl sulfate.

In another suitable embodiment, the polymers according to the invention can have both acid groups and amino groups. The difference in the number of acid groups and amino groups (|Δ No. of Ac.–No. of Am|) is here preferably in a range of from about 15 to 150, preferably from 30 to 100. In this connection, acid number and amine number are each defined as mg of KOH/g of test substance.

If, in the preparation of the polyurethanes, a water-miscible organic solvent is used, then this can be removed by customary methods known to the person skilled in the art, e.g. by distillation at reduced pressure. Prior to removal of the solvent, water can additionally be added to the polyurethane. Replacement of the solvent by water gives a solution or dispersion of the polymer, from which, if desired, the polymer can be obtained in the usual manner, e.g. by spray-drying.

The polymers according to the invention have siloxane groups. Preferably, the siloxane content based on the total weight of the incorporated components is from about 0.05 to 30% by weight, preferably from 0.05 to 25% by weight, in particular from 0.1 to 20% by weight. Their K values (measured in accordance with E. Fikentscher, Cellulose-Chemie 13 (1932), p. 58–64, using a 1% strength solution in ethanol) are generally in a range of from 15 to 90, preferably from 20 to 60. Their glass transition temperature is generally at least 0° C., particularly preferably at least 20° C. and specifically at least 30° C. If the polymers according to the invention have two or more glass transition temperatures, then at least one of them is in the given range. The other(s) is/are then below the temperature range given above.

The invention further relates to the use of water-soluble or water-dispersible polymers which are chosen from polymers according to the invention which comprise, in copolymerized form, at least one siloxane-containing urethane (meth)acrylate and at least one free-radically polymerizable α,β-ethylenically unsaturated monomer M) as described above, polymers which comprise, in copolymerized form, at least one siloxane-free urethane (meth)acrylate and at least one free-radically polymerizable α,β-ethylenically unsaturated monomer M), where the siloxane-free urethane (meth)acrylate comprises, in incorporated form, components a), b) and c), as defined above, and optionally at least one other component chosen from components e), f) and g), as defined above, and mixtures thereof in hair cosmetics, preferably as setting polymer in hairsprays, setting foams, hair mousse, hair gel and shampoos, in skin cosmetics, preferably in creams, pigment-containing skin cosmetics and wax-containing skin cosmetics, in pharmacy, preferably in coating compositions or binders for solid drug forms, and in coating compositions for the textile, paper, printing, leather and adhesives industries.

As well as the polymers according to the invention, siloxane-free polymers and mixtures of siloxane-containing and siloxane-free polymers are also preferably suitable for use in hair cosmetics, preferably as setting polymers in hairsprays, setting foams, hair mousse, hair gel and shampoos.

For the preparation of siloxane-free water-soluble or water-dispersible polymers, at least one siloxane-free urethane (meth)acrylate and at least one free-radically polymerizable α,β-ethylenically unsaturated monomer M) is subjected to free-radical copolymerization. Suitable polymerization processes are the customary processes known to the person skilled in the art. These include those described above for the preparation of the polymers according to the invention.

The preparation of suitable free-radically polymerizable, siloxane-free urethane (meth)acrylates is carried out as described above for the preparation of the siloxane-containing urethane (meth)acrylates according to the invention. It dispenses with the use of siloxane-containing components d). Components a), b), c), e), f) and g) which are suitable and preferred for the preparation are those given in accordance with the above.

The monomer M) is preferably chosen from the above-described monomers M1), M2), M3) and mixtures thereof.

The siloxane-free polymers are preferably used in hair-treatment compositions, such as setting foams, hair mousse, hair gel, shampoos and, in particular, hairsprays. Suitable components and the amounts thereof used for formulating hair-treatment compositions are those given below for hair-treatment compositions based on the siloxane-containing polymers according to the invention.

The siloxane-containing polymers according to the invention and the above-described siloxane-free polymers can be used as auxiliaries in cosmetics and pharmacy, especially as or in coating composition(s) for keratinous surfaces (hair, skin and nails) and as coating compositions and/or binders for solid drug forms. In addition, they can be used as or in coating composition(s) for the textile, paper, printing, leather and adhesives industries. They are particularly suitable for use in hair cosmetics. The abovementioned polymers can also be used in creams and as tablet coatings and tablet binders. They are also suitable as binders and adhesives for cosmetic products, e.g. in the preparation of cosmetic stick products, such as deodorant sticks, make-up sticks, etc.

The siloxane-containing polymers according to the invention and the above-described siloxane-free polymers are preferably suitable for use in skin cosmetics, preferably in creams, pigment-containing skin cosmetics and wax-containing skin cosmetics.

The present invention also relates to a cosmetic or pharmaceutical composition which comprises the polymers according to the invention. The composition generally comprises the polymers in an amount in the range from 0.2 to 30% by weight, based on the total weight of the composition.

The cosmetic compositions according to the invention are particularly suitable as coating compositions for keratinous surfaces (hair, skin and nails). The optionally neutralized or quaternized compounds used therein are water-soluble or water-dispersible. If the compounds used in the compositions according to the invention are water-dispersible, they can be used in the form of aqueous microdispersions having particle diameters of, customarily, from 1 to 250 nm, preferably from 1 to 150 nm. The solids contents in the preparations are here usually in a range of from about 0.5 to 20% by weight, preferably from 1 to 12% by weight. These microdispersions do not normally require emulsifiers or surfactants for stabilization.

The compositions according to the invention can preferably be in the form of a hair-treatment composition, such as setting foams, hair mousse, hair gel, shampoo and especially in the form of a hair spray. For use as hair-setting agents, preferred compositions are those comprising polymers having at least a glass transition temperature $T_g$ of $\geq 20°$ C., preferably $\geq 30°$ C. The K value of these polymers is preferably in a range from 23 to 90, in particular from 25 to 60. The siloxane content of these polymers is generally from 0.05 to 20% by weight, based on the total weight of the incorporated components.

The compositions are preferably hair-treatment compositions. They are usually in the form of an aqueous dispersion or in the form of an alcoholic or aqueous-alcoholic solution. Examples of suitable alcohols are ethanol, propanol, isopropanol etc.

In addition, the hair-treatment compositions according to the invention generally comprise customary cosmetic auxiliaries, for example softening agents, such as glycerol and glycol; emollients; perfumes; UV absorbers; dyes; antistatics; agents for improving combability; preservatives; and antifoams.

When formulated as hairsprays, the compositions according to the invention comprise a sufficient amount of a propellant, for example a low-boiling hydrocarbon or ether, such as propane, butane, isobutane or dimethyl ether. Compressed gases, such as nitrogen, air or carbon dioxide, can also be used as propellant. The amount of propellant can be kept low in order not to unnecessarily increase the VOC content. It is then generally no more than 55% by weight, based on the total weight of the composition. If desired, however, relatively high VOC contents of 85% by weight and above are also possible.

The above-described polyurethanes can also be used in combination with other hair polymers in the compositions. Such polymers are, in particular:

nonionic, water-soluble or water-dispersible polymers or oligomers, such as polyvinylcaprolactam, e.g. Luviskol Plus (BASF), or polyvinylpyrrolidone and copolymers thereof, in particular with vinyl esters, such as vinyl acetate, e.g. Luviskol VA 37 (BASF); polyamides, e.g. those based on itaconic acid and aliphatic diamines; polyvinyl alcohol;

amphoteric or zwitterionic polymers, such as the octylacrylamide/methyl methacrylate/tert-butylaminoethyl methacrylate/2-hydroxypropyl methacrylate copolymers obtainable under the names Amphomer® (Delft National), as disclosed, for example, in German Patent Applications DE 39 29 973, DE 21 50 557, DE 28 17 369 and DE 37 08 451. Acrylamidopropyltrimethylammonium chloride/acrylic acid or methacrylic acid copolymers and their alkali metal and ammonium salts are preferred zwitterionic polymers. Other suitable zwitterionic polymers are methacroylethyl betaine/methacrylate copolymers, which are obtainable commercially under the name Amersette® (AMERCHOL) and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are available commercially, for example, under the names Resyn® (NATIONAL STARCH), Luviset® (BASF) and Gafset® (GAF), vinylpyrrolidone/vinyl acrylate copolymers, obtainable, for example, under the trade name Luviflex®(BASF). A preferred polymer is the vinylpyrrolidone/acrylate terpolymer obtainable under the name Luviflex® VBM-35 (BASF), acrylic acid/ethyl acrylate/N-tert-butylacrylamide terpolymers, which are marketed, for example, under the name Ultrahold® strong (BASF), and Luvimer® (BASF, terpolymer of t-butyl acrylate, ethylacrylate and methacrylic acid), or cationic (quaternized) polymers, e.g. cationic polyacrylate copolymers based on N-vinyllactams and derivatives thereof (N-vinylpyrrolidone, N-vinylcaprolactam etc.) and customary cationic hair-conditioning polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers which are formed by reaction of polyvinylpyrrolidone with quaternary ammonium compounds), polymer JR (hydroxyethylcellulose containing cationic groups), polyquaternium products (CTFA names) etc.;

nonionic siloxane-containing, water-soluble or -dispersible polymers, e.g. polyether siloxanes, such as Tegopren® (Goldschmidt) or Belsil® (Wacker);

hair polymers based on nature, such as chitosan, caseine, cellulose derivatives, etc.

The polymers according to the invention can be used as a mixture with another amide-containing hair polymer. Examples thereof include the polyurethanes described in DE-A-42 25 045, the previously described vinylpyrrolidone/acrylate terpolymers and acrylic acid/ethyl acrylate/N-tert-butylacrylamide terpolymers (e.g. Ultrahold® strong from BASF AG), the above-described amide-containing amphoteric polymers (e.g. Amphomer®) and, in particular, copolymers which have a content of amide-containing monomers, such as N-vinyllactams, of at least 30% by weight (e.g. Luviskol®plus and Luviskol®VA37 from BASF AG).

The polymers according to the invention can also be used as a mixture with another siloxane-containing hair polymer, preferably siloxane-containing polyurethanes.

The other hair polymers are preferably present in amounts of up to 10% by weight, based on the total weight of the composition.

A preferred hair-treatment composition comprises:
a) from 0.5 to 20% by weight of at least one water-soluble or -dispersible polymer according to the invention,
b) from 30 to 99.5% by weight, preferably from 40 to 99% by weight, of a solvent chosen from water and water-miscible solvents, preferably $C_2$- to $C_5$-alcohols, in particular ethanol, and mixtures thereof,
c) from 0 to 70% by weight of a propellant, preferably dimethyl ether,
d) from 0 to 10% by weight of at least one water-soluble or -dispersible hair polymer which is different from a),
e) from 0 to 0.3% by weight of at least one water-insoluble silicone,
f) from 0 to 1% by weight of at least one nonionic, siloxane-containing, water-soluble or -dispersible polymer, and customary additives.

The composition according to the invention can comprise, as component d), at least one other water-soluble or -dispersible hair polymer. The content of this component is then generally from about 0.1 to 10% by weight, based on the total weight of the composition. Preference is given in this connection to using water-soluble or water-dispersible polyurethanes which comprise siloxane groups in copolymerized form.

The composition according to the invention can comprise, as component e), at least one water-insoluble silicone, in particular a polydimethylsiloxane, e.g. the Abil® products from Goldschmidt. The content of this component is then generally from about 0.0001 to 0.2% by weight, preferably from 0.001 to 0.1% by weight, based on the total weight of the composition.

The composition according to the invention can comprise, as component f), at least one nonionic, siloxane-containing, water-soluble or -dispersible polymer, in particular chosen from the above-described polyethersiloxanes. The content of this component is then generally from about 0.001 to 2% by weight, based on the total weight of the composition.

The composition according to the invention can, where appropriate, additionally comprise an antifoam, e.g. one based on silicone. The amount of the antifoam is generally up to about 0.001% by weight, based on the total amount of the composition.

The invention also relates to a hair-treatment composition comprising:
a) from 0.5 to 20% by weight of at least one water-soluble or -dispersible polymer which comprises, in copolymerized form, at least one siloxane-free urethane (meth)acrylate and at least one free-radically polymerizable $\alpha,\beta$-ethylenically unsaturated monomer M), where the siloxane-free urethane (meth)acrylate comprises, in incorporated form, components a), b) and c) as defined in claim 1 and optionally at least one other component chosen from components e), f) and g), as defined in claim 2,
b) from 30 to 99.5% by weight, preferably from 40 to 99% by weight, of at least one solvent chosen from water, water-miscible solvents and mixtures thereof,
c) from 0 to 70% by weight of a propellant,
d) from 0 to 10% by weight of at least one water-soluble or -dispersible hair polymer which is different from a),
e) from 0 to 0.3% by weight of at least one water-insoluble silicone,
f) from 0 to 1% by weight of at least one nonionic, siloxane-containing, water-soluble or -dispersible polymer.

Suitable polymers a), which comprise, in copolymerized form, at least one siloxane-free urethane (meth)acrylate and at least one free-radically polymerizable α,β-ethylenically unsaturated monomer M), and processes for their preparation are those already described above. Suitable components b), c), d), e) and f) are likewise those given above for the compositions based on siloxane-containing polymers according to the invention. Reference is made to all of the statements relating to compositions based on siloxane-containing polymers according to the invention.

The compositions according to the invention have the advantage that, on the one hand, they impart to the hair the desired hold, and on the other hand, the polymers can be washed out easily (are redispersible). Moreover, hair-treatment compositions with a VOC content of less than 85% by weight, preferably of less than 60% by weight, and also purely aqueous formulations can be prepared, even when they are formulated as hairsprays.

The invention is illustrated in more detail by reference to the nonlimiting examples below.

EXAMPLES

Urethane (meth)acrylate Preparation

To prepare the urethane (meth)acrylates in Table 1 below which comprise, in incorporated form, hydroxyl-containing components (Example 2: neopentyl glycol, Example 4: dimethylolpropanoic acid), the hydroxyl-containing component, in an amount in accordance with Table 1 in acetone (solids content of the resulting reaction solution about 80%) was introduced into a four-necked flask fitted with stirrer, dropping funnel, thermometer, reflux condenser and equipment for working under nitrogen, and heated to a temperature of 60° C. with stirring. Isophorone diisocyanate was then added dropwise with stirring in an amount in accordance with Table 1, and the reaction temperature increased. At reflux, the reaction mixture was stirred until the isocyanate group content of the mixture remained virtually constant and then cooled to room temperature with stirring. A polysiloxanediamine ($M_n$=900 g/mol, Tegomer® A—Si 2122 from Goldschmidt) and tert-butylaminoethyl methacrylate (in the form of a 50% strength by weight solution in acetone) were then added, at a temperature of about 30° C., in an amount in accordance with Table 1 to the polyurethane prepolymers prepared as described above. The mixture was then stirred for a further 20 minutes at about 50° C. and then a polyethylene glycol diamine (O,O'-bis(2-aminopropyl)polyethylene glycol 800, $M_n$=900 g/mol from Fluka, in the form of a 70% strength solution in ethanol) was added. The reaction mixture was then stirred for a further 30 minutes at 30° C.

To prepare the urethane (meth)acrylates which do not contain, in incorporated form, hydroxyl-containing components (Examples 1, 3 and 5), a mixture of a polysiloxanediamine (Examples 1 and 3: $M_n$=900 g/mol; Example 5: $M_n$=2800 g/mol), tert-butylaminoethyl methacrylate (in the form of a 50% strength by weight solution in acetone) and optionally N-methyldipropylenetriamine (Example 3) as introduced in an amount in accordance with Table 1 into the above-described apparatus and heated to about 30° C. with stirring. Isophorone diisocyanate was then added dropwise with stirring in an amount in accordance with Table 1, and then the reaction mixture was stirred at a temperature of about 30° C. until the isocyanate group content remained virtually constant. A polyethylene glycol diamine was then added likewise in an amount in accordance with Table 1 at room temperature, and the reaction mixture was stirred for a further 30 minutes at about 30° C. The reaction mixture was then diluted in each case to 50% by weight using ethanol.

TABLE 1

| Ex. No. | Polysiloxane-diamine I[1] [mol] | Polysiloxane-diamine II[2] [mol] | PEGDA[3] [mol] | NPG[4] [mol] | MADPTA[5] [mol] | DMPA[6] [mol] | tBAEMA[7] [mol] | IDPI[8] [mol] |
|---|---|---|---|---|---|---|---|---|
| 1 | 1 | — | 4.5 | — | — | — | 1 | 6 |
| 2 | 1 | — | 3.5 | 1 | — | — | 1 | 6 |
| 3 | 1 | — | 3.5 | — | 1 | — | 1 | 6 |
| 4 | 1 | — | 3.5 | — | — | 1 | 1 | 6 |
| 5 | — | 0.5 | 5 | — | — | — | 1 | 6 |

[1]Polysiloxanediamine, $M_n$ = 900 g/mol (Tegomer® A-Si 2122 from Goldschmidt)
[2]Polysiloxanediamine, $M_n$ = 2800 g/mol (Tegomer® A-Si 2322 from Goldschmidt)
[3]O,O'-Bis(2-aminopropyl)polyethylene glykol 800, $M_n$ = 900 g/mol (Fluka)
[4]Neopentyl glykol
[5]N-Methyldipropylenetriamine
[6]Dimethylolpropanoic acid
[7]tert-Butylaminoethyl methacrylate
[8]Isophorone diisocyanate

Example 6

Urethane (meth)acrylate Preparation in Ethanol

To prepare a urethane (meth)acrylate containing urea groups, a mixture of a polysiloxane amine ($M_n$=2000 g/mol, amine number about 28 (corresponding to 0.04 mol of amino groups), MAN® 00078 from Hüls) and 80 g of ethanol were introduced into a four-necked flask fitted with stirrer, dropping funnel, thermometer, reflux condenser and equipment for working under nitrogen. At a temperature of about 20° C., 133 g (approximately 0.6 mol) of isophorone diisocyanate were added dropwise with stirring, and the reaction mixture was then stirred for a further 20 minutes at ambient temperature. 7.4 g (0.04 mol) of tert-butylaminoethyl methacrylate dissolved in 100 g of ethanol were then added, followed by a mixture of 315 g (0.35 mol) of O,O'-bis(2-aminopropyl)polyethylene glycol 800 ($M_n$=900 g/mol from Fluka) and 33.5 g (0.23 mol) of N-methyldipropylenetriamine dissolved in 400 g of ethanol. A reaction temperature of no more than 40° C. was maintained. The reaction mixture was stirred for a further 30 minutes at about 40° C. and finally filtered, giving a clear, colorless 30% strength ethanolic solution of a urea-containing product.

The reaction procedure from Example 6 can be used to prepare the urethane (meth)acrylates containing urea groups of the above-described Examples 1, 3 and 5.

Examples 7 to 29

Feed 1: 220 g of monomer mixture in accordance with Table 2
Feed 2: 0.5 g of tert-butyl perpivalate 100 g of ethanol
Feed 3: 1.5 g of tert-butyl perpivalate 82 g of ethanol 44 g of Feed 1 and 12 g of Feed 2 in 120 g of ethanol were introduced into a stirred apparatus fitted with reflux condenser and two separate feed devices under a nitrogen atmosphere, and were heated to about 80° C. with stirring. After partial polymerization, recognizable when the viscosity starts to increase, the remainder of the Feed 1 was added over the course of 4 hours, and the remainder of Feed 2 was added over the course of 5 hours, the internal temperature being maintained at about 70 to 80° C. The mixture was then left to react for a further 2 hours at a temperature of from about 75 to 80° C., and then Feed 3 was added over the course of 2 hours. When the addition was complete, the mixture was after polymerized at this temperature for about a further 4 hours. The acid-containing polymers were then neutralized with a base in accordance with Table 2 and the amine-containing polymers were neutralized with an acid. The K values and degrees of neutralization of the polymers are likewise given in Table 2.

Polymers based on nonionic components or based on urethane (meth)acrylates which already carry neutralized or quaternized groups can generally be used directly for formulating hair preparations.

TABLE 2

| Ex. No. | Urethane (meth)-acrylate from Ex. No. [% by wt.] | TBA[1] [% by wt.] | MAA[2] [% by wt.] | DMAPMA[3] [% by wt.] | VP[4] [% by wt.] | VCap[5] [% by wt.] | Neutralizing agent (degree of neutralization) | K value[7] |
|---|---|---|---|---|---|---|---|---|
| 7 | (1) 10 | 65 | 25 | — | — | — | AMP[6] (95%) | 43.7 |
| 8 | (1) 20 | 60 | 20 | — | — | — | AMP (95%) | 41.9 |
| 9 | (1) 30 | 52 | 18 | — | — | — | AMP (95%) | 38.9 |
| 10 | (2) 10 | 65 | 25 | — | — | — | AMP (100%) | 45.3 |
| 11 | (3) 10 | 65 | 25 | — | — | — | AMP (100%) | 46.0 |
| 12 | (4) 10 | 65 | 25 | — | — | — | AMP (95%) | 40.1 |
| 13 | (5) 10 | 65 | 25 | — | — | — | AMP (100%) | 42.8 |
| 14 | (4) 25 | 55 | 20 | — | — | — | AMP (100%) | 39.6 |
| 15 | (1) 10 | 55 | 25 | 10 | — | — | AMP (100%) | 38.3 |
| 16 | (1) 10 | 40 | — | 15 | 35 | — | H$_3$PO$_4$ (50%) | 37.9 |
| 17 | (1) 20 | — | — | 10 | 35 | 35 | H$_3$PO$_4$ (50%) | 45.2 |
| 18 | (2) 30 | — | — | 10 | 35 | 25 | H$_3$PO$_4$ (50%) | 41.0 |
| 19 | (3) 30 | — | — | — | 35 | 35 | H$_3$PO$_4$ (30%) | 39.0 |
| 20 | (3) 30 | — | — | — | — | 70 | H$_3$PO$_4$ (30%) | 42.0 |

| Ex. No. | Urethane (meth)-acrylate from Ex. No. [% by wt.] | TBA[1] [% by wt.] | n-BA[8] [% by wt.] | NTBAM[9] [% by wt.] | MAA[2] [% by wt.] | DMAPMA[3] [% by wt.] | VP[4] [% by wt.] | VCap[5] [% by wt.] | Neutralizing agent (degree of neutralization) | K value[7] |
|---|---|---|---|---|---|---|---|---|---|---|
| 21 | (1) 10 | 30 | 35 | — | 25 | — | — | — | AMP[6] (95%) | 41.3 |
| 22 | (1) 10 | — | 45 | 20 | 25 | — | — | — | AMP (95%) | 43.7 |
| 23 | (6) 10 | 22 | 45 | — | 23 | — | — | — | AMP (95%) | 44.1 |
| 24 | (6) 10 | — | 55 | 12 | 23 | — | — | — | AMP (95%) | 45.0 |
| 25 | (1) 10 | 20 | 20 | — | — | — | 15 | — | 35 | H$_3$PO$_4$ (50%) | 38.9 |
| 26 | (1) 10 | — | 20 | 20 | — | — | 12 | — | 38 | H$_3$PO$_4$ (50%) | 37.5 |

TABLE 2-continued

| | | | | | | | | | | |
|---|---|---|---|---|---|---|---|---|---|---|
| 27 | (6) 10 | 40 | — | — | — | 15 | — | 35 | $H_3PO_4$ (50%) | 40.2 |
| 28 | (6) 10 | 20 | 20 | — | — | 12 | — | 38 | $H_3PO_4$ (50%) | 42.1 |
| 29 | (6) 10 | — | 20 | 20 | — | 15 | — | 35 | $H_3PO_4$ (50%) | 43.0 |

[1] tert-Butyl acrylate
[2] N,N-Dimethylaminopropylmethacrylamide
[3] Methacrylic acid
[4] Vinylpyrrolidone
[5] Vinylcaprolactam
[6] 2-Amino-2-methylpropanol
[7] measured as a 15% strength solution in ethanol
[8] n-Butyl acrylate
[9] N-(tert-Butyl)acrylamide

Application Examples

Examples 30 to 52

Aerosol Hairspray Formulations with a VOC Content of 97% by Weight

| | |
|---|---|
| Polymer according to Example 7-29 | 3.00% by weight |
| Ethanol | 62.00% by weight |
| Dimethyl ether | 34.96% by weight |
| Perfume, additives | q.s. |

Examples 53 to 75

Compact Aerosol Hairspray Formulations with a VOC Content of 90% by Weight

| | |
|---|---|
| Polymer according to Example 7-29 | 10.00% by weight |
| Ethanol | 55.00% by weight |
| Dimethyl ether | 34.96% by weight |
| Perfume, additives | q.s. |

Examples 76 to 98

Hairspray Formulations with a VOC Content of 80% by Weight

| | |
|---|---|
| Polymer according to Example 7-29 | 5.00% by weight |
| Ethanol | 45.00% by weight |
| Water | 15.00% by weight |
| Dimethyl ether | 34.96% by weight |
| Perfume, additives | q.s. |

Examples 99 to 121

Hairspray Formulations with a VOC Content of 55% by Weight

| | |
|---|---|
| Polymer according to Example 7-29 | 3.00% by weight |
| Ethanol | 20.00% by weight |
| Water | 42.00% by weight |
| Dimethyl ether | 34.96% by weight |
| Perfume, additives | q.s. |

Examples 122 to 137

Pump Hairspray Formulations with a VOC Content of 55% by Weight

| | |
|---|---|
| Polymer according to Example 8, 9, 14 17–29 | 10.00% by weight |
| Water | 37.00% by weight |
| Ethanol | 55.00% by weight |
| Perfume, additives | q.s. |

Examples 138 to 160

| Foam conditioner | : [% by weight] |
|---|---|
| Polymer 7-29 (25% strength aqueous solution) | 20.00 |
| Cremophor ® A[10] | 0.20 |
| Comperlan ® KD[11] | 0.10 |
| Water | 69.70 |
| Propane/butane | 9.96 |
| Perfume, preservatives | q.s. |

[10] CTFA name: Ceteareth 25, BASF AG, reaction product of fatty alcohol and ethylene oxide
[11] CTFA-Name: Cocamide DEA, Henkel, coconut fatty acid amide To prepare the foam conditioner, the components are weighed and dissolved with stirring. They are then transferred to a dispenser, and the propellant gas is added.

Examples 161 to 183

| Conditioner shampoo: | [% by weight] |
|---|---|
| A) Texapon ® NSO 28% strength[12] | 50.00 |
| Comperlan ® KD | 1.00 |
| Polymer 1-14 (25% strength aqueous solution) | 20.00 |
| Perfume oil | q.s. |

-continued

| Conditioner shampoo: | [% by weight] |
|---|---|
| B) Water | 27.5 |
| Sodium chloride | 1.5 |
| Preservatives | q.s. |

[12)]Sodium lauryl sulfate, Henkel

To prepare the conditioner shampoos, components A) and B) are separately weighed and dissolved with mixing. Phase B) is then slowly added to phase A) with stirring.

Examples of Uses in the Skin Cosmetics

Examples 184 to 206

| | % by wt. | CTFA name: |
|---|---|---|
| Oil phase: | | |
| Cremophor ® A6 (BASF AG) | 3.5 | Ceteareth-6 (stearyl alcohol ethoxylate) |
| Cremophor ® A25 (BASF AG) | 3.5 | Ceteareth-25 (fatty alcohol ethoxylate) |
| Glycerol monostearate s.e. | 2.5 | Glycerol stearate |
| Paraffin oil | 7.5 | |
| Cetyl alcohol | 2.5 | |
| Luvitol ® EHO (BASF AG) | 3.2 | Cetearyl octanoate |
| Vitamin E acetate | 1.0 | Tocopheryl acetate |
| Nip-Nip ®, Nipa Laboratories Ltd., USA | 0.1 | Methyl and propyl 4-hydroxybenzoate (7:3) |
| Water phase: | | |
| Polymer 7-29 | 1.5 | |
| Water | 73.6 | |
| 1,2-Propylene glycol | 1.0 | Propylene glycol |
| Germall II, Sutton Laboratories Inc., USA | 0.1 | Imidazolidinylurea |

To prepare the creams, the components for the oil and water phases are separately weighed and homogenized at 80° C. The water phase is then slowly added to the oil phase. The mixture is then left to cool to room temperature with stirring.

Examples 207 to 229

O/W Lotions

| | % by wt. | CTFA name: |
|---|---|---|
| Oil phase: | | |
| Cremophor ® A6 (BASF AG) | 2.0 | Ceteareth-6 (stearyl alcohol ethoxylate) |
| Cremophor ® A25 (BASF AG) | 2.0 | Ceteareth-25 (fatty alcohol ethoxylate)) |
| Glycerol monostearat s.e. | 6.0 | Glyceryl stearate |
| Paraffin oil | 0.9 | Paraffin oil |
| Tegiloxan ® 100 | 0.1 | Dimethicone (polydimethylsiloxane) |
| Cetyl alcohol | 1.5 | Cetyl alcohol |
| Luvitol ® EHO (BASF AG) | 12.0 | Cetearyl octanoate |
| Vitamin E acetate | 0.4 | Tocopheryl acetate |

-continued

| | % by wt. | CTFA name: |
|---|---|---|
| Nip-Nip ®, Nipa Laboratories Ltd., USA | 0.1 | Methyl and propyl 4-hydroxybenzoate (7:3) |
| Water phase: | | |
| Polymer 7-29 | 1.0 | |
| Water | 73.4 | |
| 1,2-Propylene glycol | 1.0 | Propylene glycol |
| Germall II, Sutton Laboratories Inc., USA | 0.1 | Imidazolidinylurea |

To prepare the O/W lotions, the components for the oil and water phases are separately weighed and homogenized at 80° C. The water phase is then slowly added to the oil phase with stirring. The mixture is then left to cool to room temperature with stirring.

We claim:

1. A hair-treatment or skin cosmetic composition which comprises at least one water-soluble or water-dispersible polymer and at least one cosmetic auxiliary selected from softening agents, emolients, perfumes, UV absorbers, dyes, antistatics, agents for improving combability, preservatives, and antifoams, the polymer comprising the copolymerization product of at least one urethane (meth)acrylate and at least one free-radically polymerizable, $\alpha,\beta$-ethylenically unsaturated monomer M) and the urethane (meth)acrylate being selected from free-radically polymerizable, siloxane-containing urethane (meth)acrylates that are synthesized from a) at least one compound which contains at least one active hydrogen atom and at least one free-radically polymerizable $\alpha,\beta$-ethylenically unsaturated double bond per molecule, b) at least one diisocyanate, c) at least one compound which contains two active hydrogen atoms per molecule, d) at least one compound which contains at least one active hydrogen atom and at least one siloxane group per molecule, and the salts thereof.

2. A composition as claimed in claim 1, wherein the urethane (meth)acrylate polymer which further includes in the polymer copolymerized therein, at least one component selected from e) compounds which contain two or more active hydrogen atoms and at least one ionogenic and/or ionic group per molecule, f) monohydric alcohols, amines with a primary or secondary amino group, aliphatic, cycloaliphatic or aromatic monoisocyanates and mixtures thereof, g) $\alpha,\beta$-ethylenically unsaturated compounds which additionally contain at least one isocyanate group per molecule, and mixtures thereof.

3. A composition as claimed in claim 1, wherein component d) is selected from:

polysiloxanes in the formula I.1

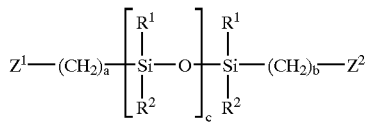
(I.1)

in which
a and b independently of one another are from 2 to 8,
c is from 3 to 100,
$R^1$ and $R^2$ independently of one another are $C_1$–$C_8$-alkyl, benzyl or phenyl,
$Z^1$ and $Z^2$ independently of one another are OH, $NHR^3$ or a radical of the formula II

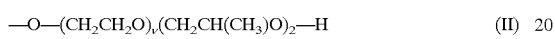
(II)

where
in formula II the order of the alkylene oxide units is arbitarry, and v and w independently of one another are an integer from 0 to 200, the sum v+w being >0,
$R^3$ is hydrogen, $C_1$–$C_8$-alkyl or $C_5$–$C_8$-cycloalkyl;

polysiloxanes of the formula I.2

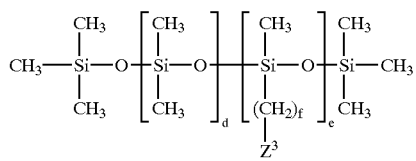
(I.2)

in which
the order of the siloxane units is arbitrary,
d and e independently of one another are from 0 to 100, the sum d+e being at least 2,
f is an integer from 2 to 8
$Z^3$ is OH, $NHR^3$ or a radical of the formula II
where $R^3$ is hydrogen, $C_1$- to $C_8$-alkyl, $C_1$- to $C_8$-cycloalkyl or a radical of the formula —$(CH_2)_u$—$NH_2$, where u is an integer from 1 to 10, polysiloxanes containing repeating units of the formula I.3

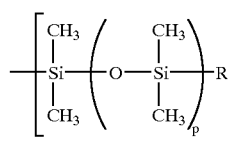
(I.3)

in which
p is an integer from 0 to 100,
q us an integer from 1 to 8,
$R^{20}$ and $R^{21}$ independently of one another are $C_1$- to $C_8$-alkylene, the order of the alkylene oxide units is arbitary and r and s independently of one another are an integer from 0 to 200, the sum r+s being >0, polysiloxanes of the formula I.4

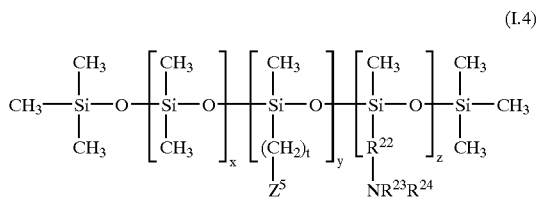
(I.4)

in which
$R^{22}$ is a $C_1$- to $C_8$-alkylene radical,
$R^{23}$ and $R^{24}$ independently of one another are hydrogen, $C_1$- to $C_8$-alkyl or $C_5$- to $C_8$-cycloalkyl, the order of the siloxane units is arbitarry,
x, y and z independently of one another are from 0 to 100, the sume x+y+z being at least 3,
t is an integer from 2 to 8,
$Z^5$ is a radical of the formula VII

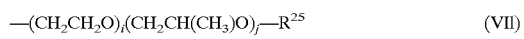
(VII)

in which
the order of the alkylene oxide is arbitrary and i and j independently of one another are an integer from 0 to 200, the sume i+j being >0,
$R^{25}$ is hydrogen or a $C_1$- to $C_8$-alkyl radical wherein at least one of the radicals $R^{23}$ $R^{24}$ or $R^{25}$ is hydrogen,
and mixtures thereof.

4. A composition as claimed in claim 1, wherein the monomer M) is chosen from

M1) essentially hydrophobic, nonionic compounds, selected from esters of α,β-ethylenically unsaturated mono- and/or dicarboxylic acids with $C_1$–$C_{30}$-alkanols, amides of α,β-ethylenically unsaturated mono- and/or dicarboxylic acids with mono- and di-$C_1$-$C_{30}$-alkylamines, esters of vinyl alcohol and allyl alcohol with $C_1$–$C_{30}$-monocarboxylic acids, vinyl ethers, vinylaromatics, vinyl halides, vinylidene halides, $C_2$–$C_8$-monoolefins, nonaromatic hydrocarbons having at least 2 conjugated double bonds and mixtures thereof, M2) compounds containing a free-radically polymerizable α,β-ethylenically unsaturated double bond and at least one ionogenic and/or ionic group per molecule, M3) essentially hydrophilic, nonionic compounds, selected from N-vinylamides, N-vinyllactams, primary amides of α,β-ethylenically unsaturated monocarboxylic acids, vinyl- and allyl-substituted heteroaromatic compounds, esters of α,β-ethylenically unsaturated mono- and dicarboxylic acids with $C_1$–$C_{30}$-alkanediols, esters and amides of α,β-ethylenically unsaturated mono- and dicarboxylic acids with $C_2$–$C_{30}$-amino alcohols which have a primary or secondary amino group, polyether acrylates, and mixtures thereof.

5. A composition as claimed in claim 1, wherein the polymer comprises, in copolymerized form, from 0.05 to 80% by weight, preferably form 0.1 to 50% by weight, of the urethane (meth)acrylates, and from 20 to 99.95% by weight, preferably from 50 to 99% by weight, of at least one component M).

6. A composition as claimed in claim 1, wherein the polymer comprises, in copolymerized form, from 0.1 to 50% by weight, preferably from 0.5 to 35% by weight, of the urethane (meth)acrylates, from 40 to 75% by weight, preferably from 45 to 73% by weight, of at least one component M1), from 10 to 35% by weight, preferably from 18 to 30%, by weight of at least one component M2), from 0 to 30% by weight of at least one component M3).

7. A composition as claimed in claim 1, wherein the polymer comprises, in copolymerized form, from 0.1 to 50% by weight, preferably from 0.5 to 35% by weight, of the urethane (meth)acrylates, from 0 to 50% by weight of at least one component M1), from 0 to 20% by weight of at least one component M2), from 25 to 80% by weight of at least one component M3).

8. A hair-treatment composition as claimed in claim 1, comprising a) from 0.5 to 20% by weight of at least one water-soluble or -dispersible polymer, b) from 30 to 99.5% by weight, preferably from 40 to 99% by 45 weight, of at least one solvent chosen from water, water-miscible solvents and mixtures thereof, c) from 0 bis 70% by weight of a propellant, d) from 0 to 10% by weight of at least one water-soluble or -dispersible hair polymer which is different from a), e) from 0 to 0.3% by weight of at least one water-insoluble, silicone, f) from 0 to 1% by weight of at least one nonionic, siloxane-containing, water-soluble or -dispersible polymer.

9. A hair treatment composition as claimed in claim 1 in the form of a hairspray, setting foam, hair mousse, hair gel or shampoo.

10. A skin cosmetic as claimed in claim 1 in the form of a cream, pigment-containing skin cosmetic or wax-containing skin cosmetics.

11. The composition of claim 1, wherein component a) is tert-butylaminoethyl acrylate and/or tert-butylaminoethyl methacrylate.

* * * * *

UNITED STATES PATENT AND TRADEMARK OFFICE
CERTIFICATE OF CORRECTION

PATENT NO. : 6,524,564 B1
DATED : February 25, 2003
INVENTOR(S) : Kim et al.

It is certified that error appears in the above-identified patent and that said Letters Patent is hereby corrected as shown below:

Column 35,
Line 24, "arbitarry" should be -- arbitrary --.
Line 47, "$C_1$- to" should be -- $C_5$- to --.
Lines 48-49, "—$(CH_2)_u$—$NH_2$" should be -- —$(CH_2)_u$—$NH_2$ --.
Line 63, "q us an" should be -- q is an --.
Lines 64-65, $C_1$- $_{to}$ $c_8$-alkylene" should be -- $C_1$- to $C_8$-alkelene --.

Column 36,
Line 16, "arbitarry" should be -- arbitrary --.
Lines 18 and 27, "sume" should be -- sum --.

Signed and Sealed this

Seventeenth Day of June, 2003

JAMES E. ROGAN
*Director of the United States Patent and Trademark Office*